United States Patent
Miura et al.

(10) Patent No.: US 9,405,394 B2
(45) Date of Patent: Aug. 2, 2016

(54) APPLICATION OPERATION EVALUATING APPARATUS AND APPLICATION OPERATION EVALUATING METHOD

(71) Applicant: SHISEIDO COMPANY, LTD., Tokyo (JP)

(72) Inventors: Yoshimasa Miura, Kanagawa (JP); Sayaka Suzuki, Kanagawa (JP); Naruhito Toyoda, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/382,124

(22) PCT Filed: Feb. 28, 2013

(86) PCT No.: PCT/JP2013/055444
§ 371 (c)(1),
(2) Date: Aug. 29, 2014

(87) PCT Pub. No.: WO2013/129582
PCT Pub. Date: Sep. 6, 2013

(65) Prior Publication Data
US 2015/0054758 A1 Feb. 26, 2015

(30) Foreign Application Priority Data

Mar. 2, 2012 (JP) .................................. 2012-047058
Feb. 25, 2013 (JP) .................................. 2013-034865

(51) Int. Cl.
*G06F 3/041* (2006.01)
*G06F 3/0354* (2013.01)
(Continued)

(52) U.S. Cl.
CPC ............. *G06F 3/0414* (2013.01); *G01L 1/205* (2013.01); *G01L 25/00* (2013.01); *G01N 17/004* (2013.01); *G06F 3/03547* (2013.01)

(58) Field of Classification Search
CPC ... G06F 3/0414; G06F 3/0416; G06F 3/0488; G01L 1/205; G01L 25/00; G01N 17/004
USPC .................................................. 345/173–174
See application file for complete search history.

(56) References Cited

U.S. PATENT DOCUMENTS 3,657,475 A    4/1972 Peronneau et al.
4,953,410 A    9/1990 Tabota
(Continued)

FOREIGN PATENT DOCUMENTS

EP     0595746       5/1994
JP     H02-059633    2/1990
(Continued)

OTHER PUBLICATIONS

Toyada S, JP 2012-037626 A, machine translation.*
(Continued)

*Primary Examiner* — Lun-Yi Lao
*Assistant Examiner* — Peter D McLoone
(74) *Attorney, Agent, or Firm* — IPUSA, PLLC

(57) ABSTRACT

An application operation evaluating apparatus, includes a detecting unit that detects pressing force obtained by a plurality of sensors provided at an application target surface in accordance with an application operation to the application target surface; an estimating unit that estimates a pressed position of the application operation on the application target surface based on pressing forces respectively applied to the sensors obtained by the detecting unit; a load distribution generating unit that generates load distribution in accordance with the application operation based on the pressing force obtained by the detecting unit and the pressed position obtained by the estimating unit; and a display unit that displays the load distribution obtained by the load distribution generating unit on a screen.

20 Claims, 14 Drawing Sheets

(51) Int. Cl.
*G01N 17/00* (2006.01)
*G01L 25/00* (2006.01)
*G01L 1/20* (2006.01)

(56) References Cited

U.S. PATENT DOCUMENTS

| | | | | |
|---|---|---|---|---|
| 5,903,229 | A * | 5/1999 | Kishi | G06F 3/04883 178/19.01 |
| 5,959,615 | A * | 9/1999 | Yamade | G06F 3/04847 345/173 |
| 6,215,901 | B1 * | 4/2001 | Schwartz | G06K 9/222 382/186 |
| 7,898,381 | B2 | 3/2011 | Hatsuda | 338/47 |
| 7,937,227 | B2 | 5/2011 | Miura et al. | |
| 8,025,504 | B2 * | 9/2011 | Freeman | G09B 5/02 434/155 |
| 8,049,179 | B2 | 11/2011 | Miura et al. | |
| 8,264,470 | B2 * | 9/2012 | Sakurai | A61B 5/7475 345/173 |
| 8,337,554 | B2 | 12/2012 | Miura et al. | |
| 8,777,626 | B2 * | 7/2014 | Levy | G09B 17/006 434/156 |
| 8,884,870 | B2 * | 11/2014 | Grant | G06F 3/0483 345/156 |
| 2002/0149571 | A1 | 10/2002 | Roberts | |
| 2004/0141648 | A1 * | 7/2004 | Dodge | G06K 9/222 382/188 |
| 2004/0148089 | A1 * | 7/2004 | Schmidt | G06F 3/0414 701/124 |
| 2008/0048991 | A1 * | 2/2008 | Freeman | G09B 5/02 345/173 |
| 2009/0256807 | A1 | 10/2009 | Nurmi | |
| 2010/0012850 | A1 * | 1/2010 | Miura et al. | 250/372 |
| 2010/0045623 | A1 * | 2/2010 | Sakurai | A61B 5/7475 345/173 |
| 2010/0134236 | A1 * | 6/2010 | Hatsuda | 338/47 |
| 2010/0256924 | A1 * | 10/2010 | Miura et al. | 702/30 |
| 2011/0032211 | A1 | 2/2011 | Christoffersen | |
| 2011/0098815 | A1 * | 4/2011 | Miura et al. | 623/15.12 |
| 2011/0117526 | A1 * | 5/2011 | Wigdor | G09B 13/00 434/118 |
| 2011/0117535 | A1 * | 5/2011 | Benko | G06F 3/04883 434/365 |
| 2012/0022472 | A1 | 1/2012 | Miura et al. | |
| 2012/0109300 | A1 * | 5/2012 | Miura et al. | 623/15.12 |
| 2012/0212434 | A1 * | 8/2012 | Bluemler | A61M 1/14 345/173 |
| 2013/0120307 | A1 * | 5/2013 | Tsai | G06F 3/0414 345/174 |

FOREIGN PATENT DOCUMENTS

| | | |
|---|---|---|
| JP | H09-168529 | 6/1997 |
| JP | 2005-127717 | 5/2005 |
| JP | 2006-233367 | 9/2006 |
| JP | 2008-064609 | 3/2008 |
| JP | 2008-096151 | 4/2008 |
| JP | 4365452 | 11/2009 |
| JP | 4454695 | 4/2010 |
| JP | 2012-037626 | 2/2012 |
| WO | 2010018889 | 2/2010 |
| WO | 2010/113961 | 10/2010 |

OTHER PUBLICATIONS

Extended European Search Report dated Feb. 19, 2015.
International Search Report mailed on Apr. 16, 2013.
"Cosmetics—Sun protection test methods—In vivo determination of the sun protection factor (SPF)", International Standard, Nov. 15, 2010, ISO 24444.
Ferrero L. et al., Importance of Substrate Roughness for In Vitro Sun Protection Assessment, IFSCC Magazine, vol. 9, No. 2, 2-13 (2006).
Stanfield J. W. et al., Optimizing in vitro Measurement of Sunscreen Protection, SOFW-Journal, 7, 19-23 (2006).
Extended European Search Report dated May 4, 2015 (Replaces previous search report dated Feb. 19, 2015).

* cited by examiner

FIG.11
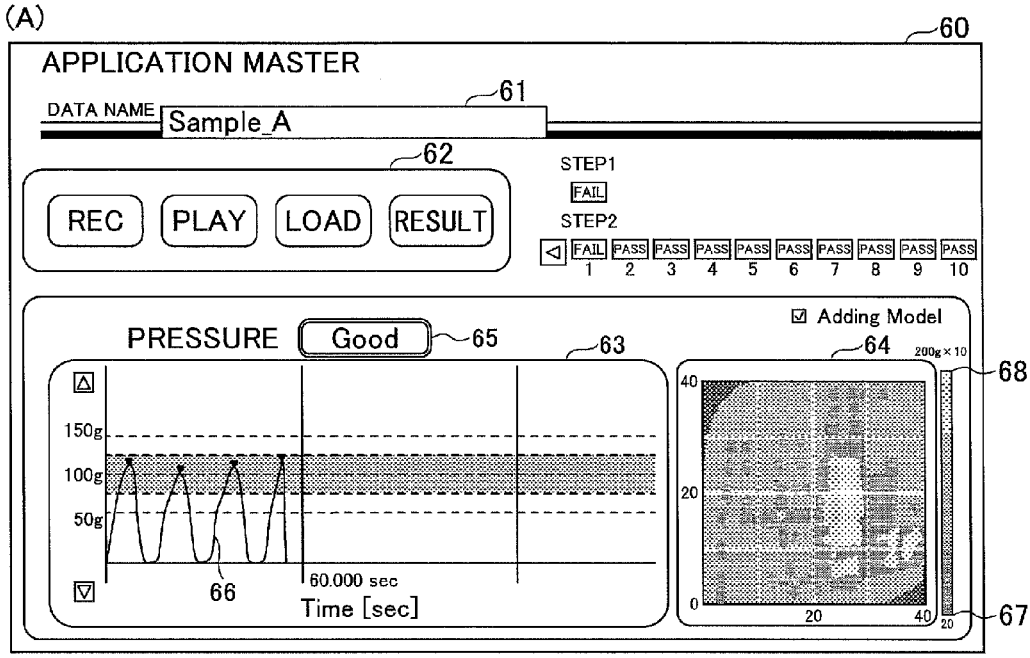
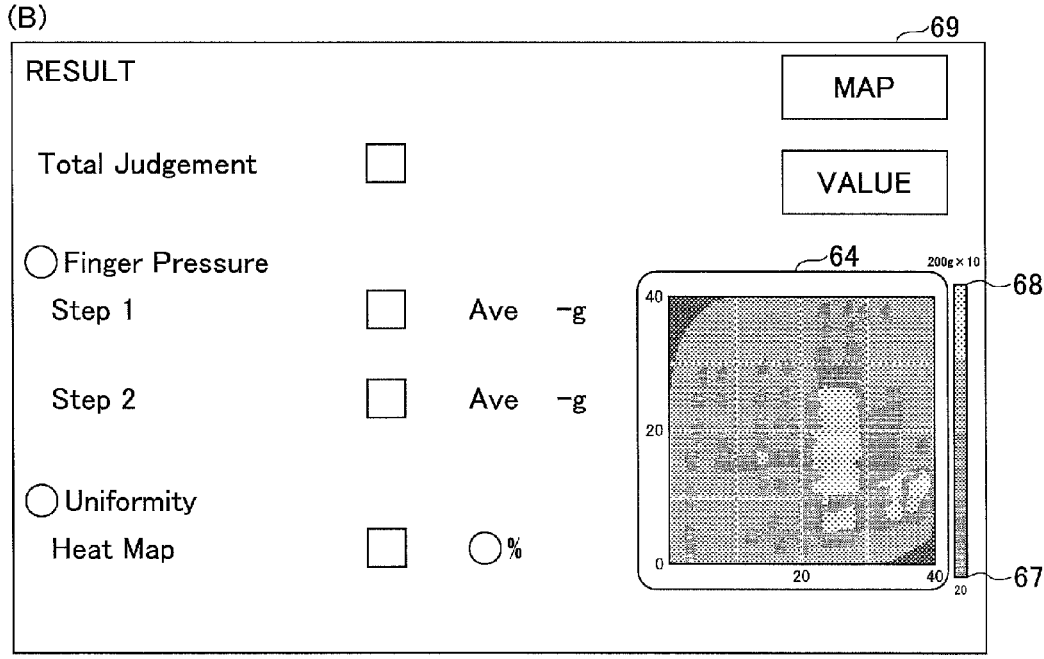

FIG.12
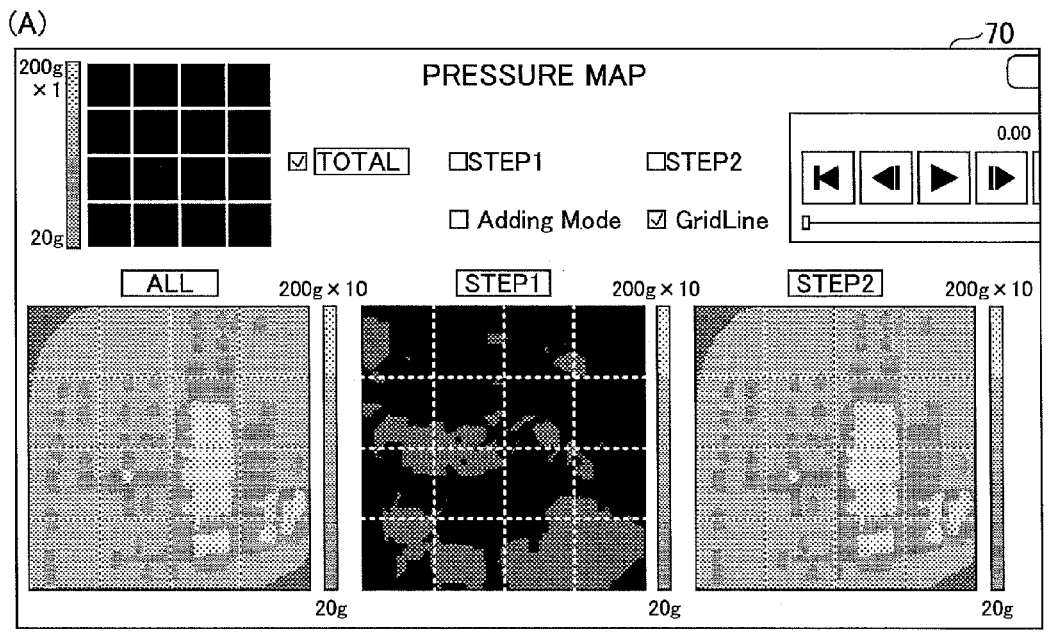
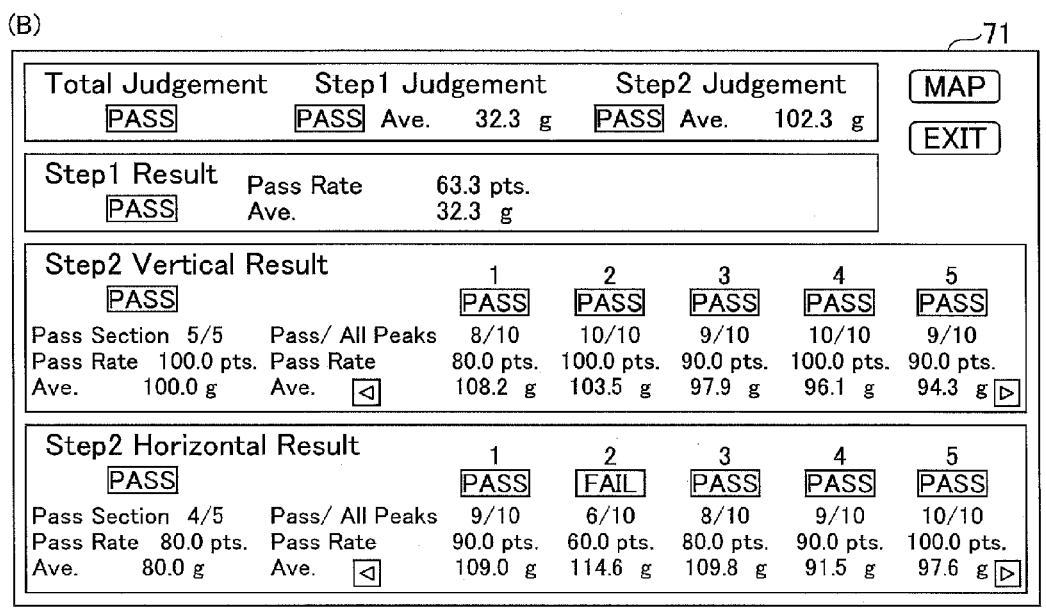

FIG.13

| | Sample | Sample A |   |   |   |
|---|---|---|---|---|---|
| | APPLICATION SUBSTRATE | SPF MASTER PA-01 | | | |
| 1 | APPLICATION PRESSURE (g)<br>*in vitro* SPF | 25g<br>39.00±5.37 | 100g<br>29.40±3.13 | 200g<br>23.22±6.11 | |
| 2 | SPEED (seconds)<br>*in vitro* SPF | 0.25<br>23.56±5.01 | 0.5<br>29.40±3.13 | 1<br>29.87±3.86 | |
| 3 | PLATE SUPPORT<br>*in vitro* SPF | Hold<br>23.34±6.71 | Fixed<br>29.40±3.13 | –<br>– | |
| 4 | APPLICATION TIME (seconds)<br>*in vitro* SPF | 30<br>24.53±3.34 | 60<br>29.40±3.13 | 90<br>19.72±0.98 | |

APPLICATION OPERATION EVALUATING APPARATUS AND APPLICATION OPERATION EVALUATING METHOD

BACKGROUND OF THE INVENTION

1. Field of the Invention

The present invention relates to an application operation evaluating apparatus and an application operation evaluating method.

2. Description of the Related Art

Sun protection cosmetics are known as functional cosmetics specified to protect against ultraviolet light. Generally, for evaluation of ultraviolet light protecting effects, numerical index, typically a Sun Protection Factor value (SPF), is used, and consumers buy a product indicated with an appropriate value in accordance with the conditions of actual, use.

The SPF value is a value based on an "ISO in vivo SPF measuring method" (see non-Patent Document 1, for example) or the like and is obtained by an in vivo measuring method using skin of a human test subject. In the in vivo SPF measurement, the measurement is conducted under a condition that a professional engineer (applier) applies a predetermined amount of sun protection cosmetic on the skin by using his/her "finger". The reason that the applier uses his/her finger in the measurement is to approximate the applied condition on the skin as the consumers mainly use their fingers when actually using the sun protection cosmetic.

However, even when the same sample is applied, if certain repeatability cannot be obtained for the applied conditions, the same measurement result cannot he obtained. Thus, it is required for the professional engineer to actualize the applied conditions with certain repeatability. Further, even when a specific applier (professional engineer) can give high repeatability to the same sample, other appliers may not be able to give the same repeatability. Thus, in order to increase reliability of the measurement results for the in vivo SPF measurement, it is required to increase the repeatability of the applied conditions not only for a certain applier but for multiple appliers.

Here, "to increase the repeatability of the applied conditions" means to actualize the same predetermined applied condition every time. This means that the thickness of the sample on an applied surface is uniform at every time, and the same measurement result is obtained at any position on the applied surface. The actual thickness of the applied sample depends on the ratio remained in the ingredient. For example, the thickness becomes an order of micron based on the sample applied amount (2.00 $mg/cm^2$) defined by the in vivo SPF measurement method, and it is not easy to apply the sample of this thickness to be uniform on the applied surface by a finger.

Further, recently, an in vitro SPF measurement has been provided (see Patent Documents 2 and 3 and non-Patent Document 3, for example) by which an SPF value of the sample is predicted by a physical measurement using an application substrate that is a substitute for skin (see Patent Document 1 and non-Patent Document 2, for example), without using skin of a test subject. This method is often used at a development stage as this measurement can be easily conducted within a short time with a lower cost.

However, the in vitro SPF measurement is a method for predicting a result of the in vivo SPF measurement, and a sample is applied using a "finger" following the in vivo SPF measurement when applying the sample on the above described application substrate. Thus, at the in vitro SPF measurement and at the in vivo SPF measurement, the above described repeatability of the applied conditions is required.

Recently, improvement of the repeatability has been provided by standardizing details of the application method (see Patent Document 4, for example).

RELATED ART

Patent Document

[Patent Document 1] Japanese Patent No. 4,454, 695
[Patent Document 2] Japanese Laid-open Patent Publication No. 2008-096151
[Patent Document 3] Japanese Patent No. 4,365,452
[Patent Document 4] PCT International Patent Publication No. 2010/113961

Non-Patent Document

[non-Patent Document 1] ISO 24444, INTERNATIONAL STANDARD, Cosmetics-Sun protection test methods-In vivo determination of the sun protection factor (SPF) [non-Patent Document 2] Ferrero L. et al., Importance of Substrate Roughness fox In vitro Sun Protection Assessment, IFSCC Magazine, Vol. 9, No. 2, 2-13 (2006) [non-Patent Document 3] Stanfield J. W. et al., Optimizing in vitro measurement of Sunscreen Protection, SOFW-Journal, 7, 19-23 (2006)

However, there are no scientifically studied cases for the repeatability of the application method and the application of the sun protection cosmetic. For example, in the above described Patent Document 4, although the improvement of the repeatability by standardizing the details of the application method is provided, factors that influence the repeatability are not revealed. Thus, at the in vitro SPF measurement and at the in vivo SPF measurement, it is required for the applier to have quite a lot of trainings in order to acquire the application method for improving the above described repeatability within each applier or among different appliers.

SUMMARY OF THE INVENTION

The present invention is made in light of. the above problems, and provides an application operation evaluating apparatus, an application operation evaluating method and an application operation evaluating program capable of improving repeatability regarding an application operation.

According to an embodiment, there is provided an application operation evaluating apparatus, including a detecting unit that detects pressing force obtained by a plurality of sensors provided at an application target surface in accordance with an application operation to the application target surface; an estimating unit that estimates a pressed position of the application operation on the application target surface based on pressing forces respectively applied to the sensors obtained by the detecting unit; a load distribution generating unit that generates load distribution in accordance with the application operation based on the pressing force obtained by the detecting unit and the pressed position obtained by the estimating unit; and a display unit that displays the load distribution obtained by the load distribution generating unit on a screen.

It is possible to improve the repeatability regarding the application operation.

BRIEF DESCRIPTION OF THE DRAWINGS

FIG. 11 is a view illustrating an example of a display screen displayed during an application operation;

FIG. 12 is a view illustrating an example of a display screen showing the load distribution and the result of each step;

FIG. 13 is a view illustrating a relationship between each application operation and an in vitro SPF predicted value;

DETAILED DESCRIPTION OF THE PREFERRED EMBODIMENTS

The invention will be described herein with reference to illustrative embodiments.
(Embodiments)

As described above, as one of conditions to improve the repeatability of the applied conditions, it is required to apply a sample with uniform thickness. The present inventors have found that, after measuring many points of an applied surface on which a sample is applied with predetermined application force by a spectrometry apparatus, for example, applying the uniform thickness can be obtained by applying the sample by uniform application force. According to the embodiment, the above described application of the uniform thickness is actualized and the repeatability of the applied conditions is improved by measuring application forces in an application operation and evaluating the application operation to apply a sample with uniform application forces.
(Schematic View of Application Operation Evaluating Apparatus)

Figure 1:
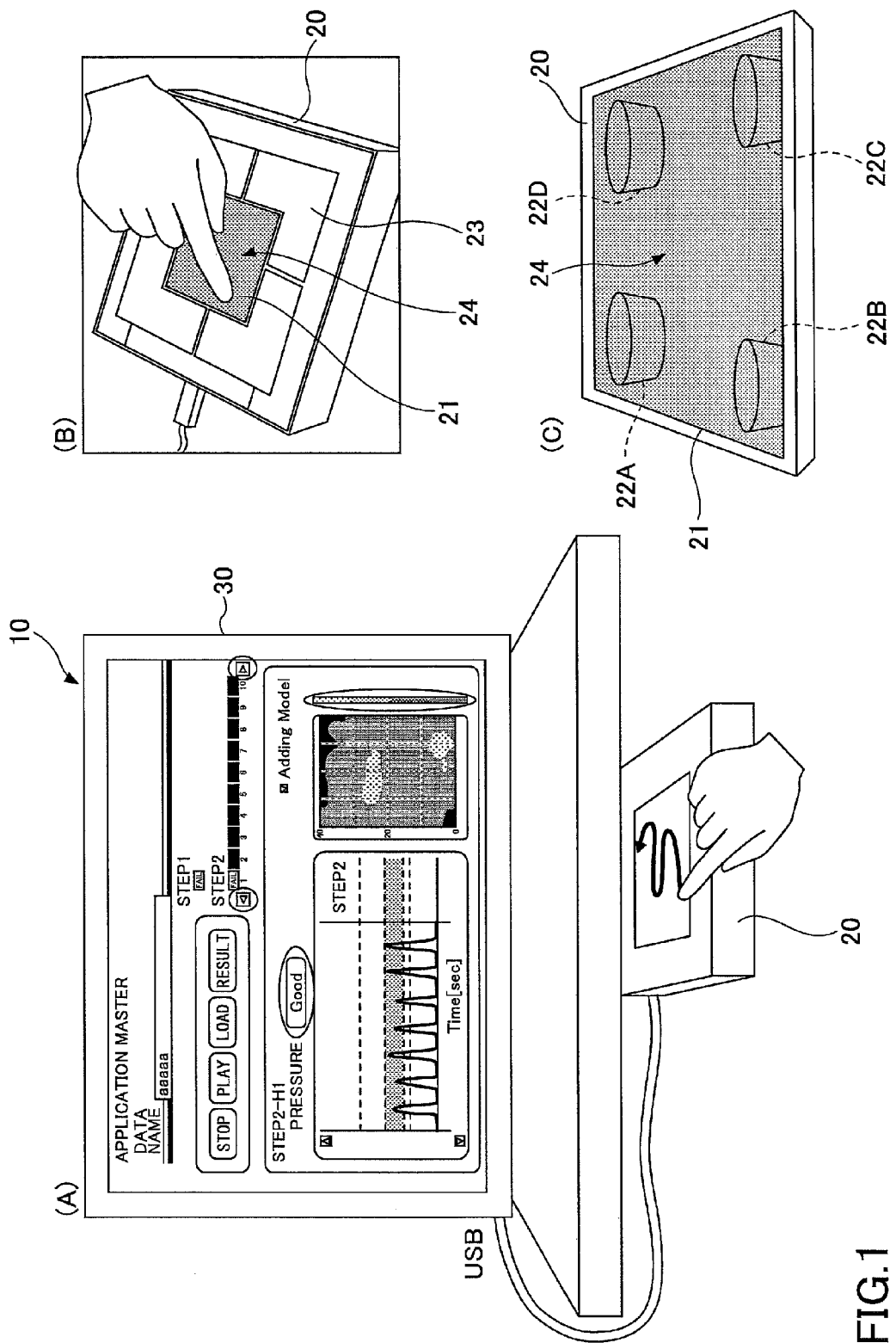
FIG. 1 is a schematic view illustrating an application operation evaluating apparatus of an embodiment.

FIG. 1 is a schematic view illustrating an application operation evaluating apparatus of the embodiment. In FIG. 1, (A) illustrates an entirety of the application operation evaluating apparatus. In FIG. 1, (B) illustrates an application operation on an application target surface. In FIG. 1, (C) illustrates sensors placed at the application target surface.

Although a sun protection cosmetic (sunscreen) is exemplified as an example of a skin lotion to be applied on the application target surface in this embodiment, this is not limited so. For example, a make-up cosmetic, a skin care cosmetic or the like may be used. Further, for the application operation on the application target surface, an operation of applying a predetermined amount of a sample of a sun protection cosmetic that uses a finger or a finger cot (finger sack) is exemplified, for example, following the in vivo SPF measurement method. However, this is not limited so and the application operation may be an operation that does not use skin lotion. For example, an application operation evaluating apparatus 10 of the embodiment may be used for evaluating an application operation when applying various materials other than the skin lotion.

As illustrated in (A) to (C) of FIG. 1, the application operation evaluating apparatus 10 includes a sensor unit 20 that detects a pressing force (application force) in accordance with an application operation, and a display unit 30 that processes pressing force data detected by the sensor unit 20 and displays generated images.

The sensor unit 20 includes an application substrate 21, sensors 22 and a position regulating member 23 that regulates the position of the application substrate 21.

The application substrate 21 is a skin substitute film (plate) that copies sulcus cutis and crista cutis of a predetermined portion. For the application substrate 21, "SPF MASTER PA01" or the like may be used, for example, but this is not limited so.

The application substrate 21 is placed on a plate member or the like provided on the sensors 22 and the position of the application substrate 21 is regulated by the position regulating member 23 such as a magnet or the like. An application target surface 24 of the application substrate 21 has a size about 5×5 cm, for example, but this is not limited so. In this embodiment, an application operation of applying a sample on the application target surface 24 is performed by a finger of a user, finger cot or the like.

The sensors 22 include four sensors 22A to 22D, for example. The sensors 22 are placed at four corners of a lower surface of the application target surface 24, for example. Each of the sensors 22 is a strain gauge, a load cell, or the like, for example and measures variation of a pressing force (micro load) applied to the respective sensor 22A to sensor 22D. The sensors 22 may be composed of three sensors, for example, by changing the arrangement.

The display unit 30 may display the pressing force that varies in accordance with time by the application operation to the application target surface 24 by the user on a screen by a sequentially display mode, or may display load distribution on a screen by an accumulated display mode, by storing the pressing force that varies in accordance with time in a memory or the like provided inside the application operation evaluating apparatus 10. Further, the display unit 30 displays various setting screens or the like for evaluating the application operation by the user using the application operation evaluating apparatus 10.
(Application Operation Evaluating Apparatus: Example of Functional Structure)

Figure 2:
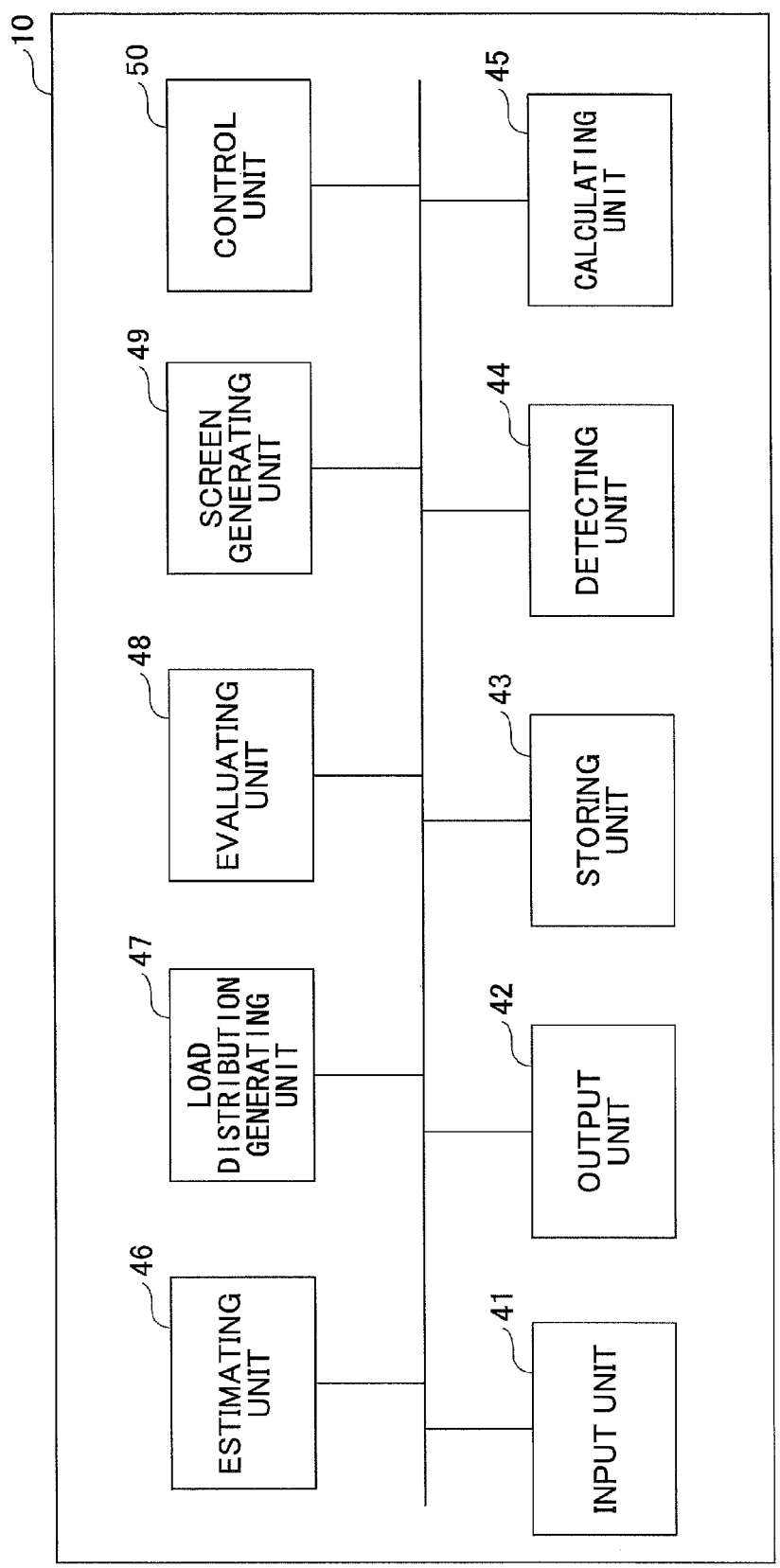
FIG. 2 is a view illustrating an example of a functional structure of the application operation evaluating apparatus of the embodiment.

Next, a functional structure of the application operation evaluating apparatus 10 is explained. FIG. 2 illustrates an example of a functional structure of the application operation evaluating apparatus of the embodiment.

As illustrated in FIG. 2, the application operation evaluating apparatus 10 includes an input unit 41, an output unit 42, a storing unit 43, a detecting unit 44, a calculating unit 45, an estimating unit 46, a load distribution generating unit 47, an evaluating unit 48, a screen generating unit 49 and a control unit 50.

The input unit 41 includes a pointing device or the like such as a keyboard, a mouse or the like, for example, and accepts input of starting or ending various instructions or the like.

The output unit 42 includes a display, a speaker or the like, for example, and displays, outputs sound or the like of a content input by the input unit 41, a content executed based on the input content or the like. The output unit 42 corresponds to the display unit 30 illustrated in FIG. 1, for example, and displays the load distribution obtained by the load distribution generating unit 47 on a screen, or displays various screens generated by the screen generating unit 49.

The storing unit 43 stores pressing forces applied to the sensors 22A to 228 obtained by the detecting unit 44 and a pressed position estimated by the estimating unit 46. Further, the storing unit 43 may store the calculated result or the like calculated by the calculating unit 45, or a previously set appropriate value of the pressing force.

The detecting unit 44 corresponds to the sensor unit 20 illustrated in FIG. 1, for example. The detecting unit 44 detects a pressing force by processing data obtained from the plurality of sensors 22 placed at the application target surface 24 in accordance with the application operation to the application target surface 24. The detecting unit 44 detects the pressing force resulting from an application operation that uses a finger or a finger cot against the application target surface 24, or the pressing force resulting from the application operation of applying a skin lotion provided on the application target surface 24.

The calculating unit 45 obtains the pressing force obtained by the detecting unit 44 every 20 ms, for example, and calculates a peak value of the pressing force within each predetermined time (0.5 seconds, for example). The method of calculating is not limited so, and the calculating unit 45 may calculate an average value of the pressing forces within each predetermined time. Further, the time interval for obtaining the pressing force is not limited to the above described 20 ms, and may be varied in accordance with the difference in the application operation or the like, for example.

The estimating unit 46 estimates the pressed position of the application operation at the application target surface 24 based on the pressing forces respectively applied to the sensors 22 obtained by the detecting unit 44. The pressed position estimating method by the estimating unit 46 is explained later.

The load distribution generating unit 47 generates load distribution caused by the application operation to the application target surface 24 based on the pressing forces obtained by the detecting unit 44 and the pressed position obtained by the estimating unit 46 at real time. The load distribution generating unit 47 previously sets color data corresponding to the load, and generates color distribution at the corresponding pressed position on the application target surface 24 based on the load data by the pressing forces obtained by the detecting unit 44, for example.

The data of the pressed position is obtained from the estimating unit 46. The load distribution generating unit 47 generates the load distribution (accumulated color distribution) using an accumulated value that is obtained by accumulating the pressing forces stored in the storing unit 43 for each pressed position, for example.

The evaluating unit 48 compares the peak value or the average value of the pressing forces within the predetermined time obtained by the calculating unit 45 with a previously set appropriate value and evaluates the application operation based on the compared result.

The screen generating unit 49 generates various screens for processing the evaluation of the application operation of the embodiment or a screen for the processed result or the like. The screen generating unit 49 outputs the generated screens to the output unit 42 or the like.

The control unit 50 controls the entirety of components of the application operation evaluating apparatus 10. The control unit 50 controls the detecting unit 44, the estimating unit 46, the load distribution generating unit 47 and the like based on the instruction from the input unit 41 by the user or the like, for example.

(Application Operation Evaluating Apparatus: Example of Hardware Structure)

Figure 3:
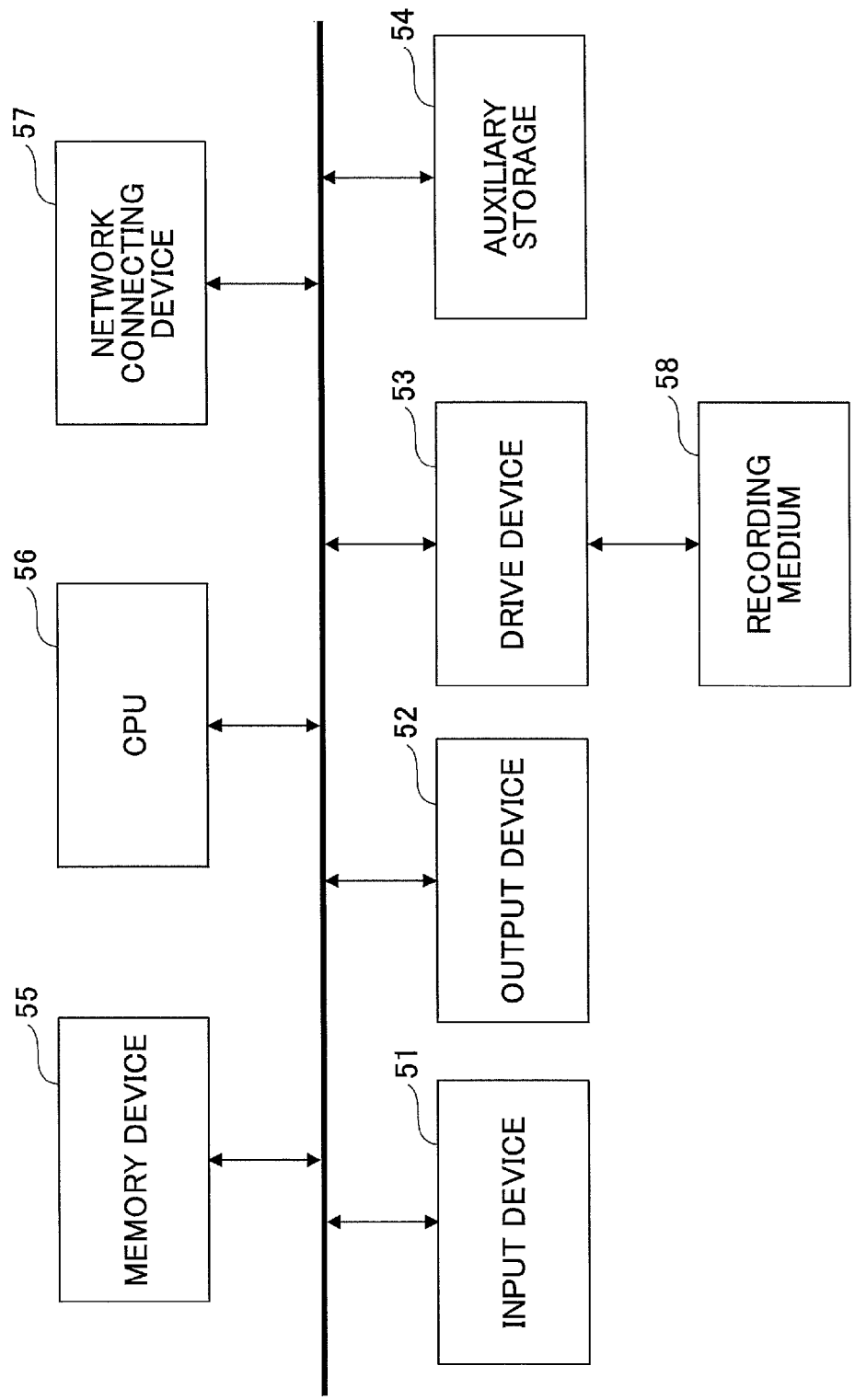
FIG. 3 is a view illustrating an example of a hardware structure of the application operation evaluating apparatus of the embodiment.

The above configuration of the application operation evaluating apparatus 10 can be performed by generating an application operation evaluating program for having a computer execute each function and installing the program in a general personal computer, a server or the like, for example. FIG. 3 is a view illustrating an example of a hardware structure of the application operation evaluating apparatus of the embodiment.

As illustrated, in FIG. 3, the application operation evaluating apparatus 10 includes an input device 51, an output device 52, a drive device 53, an auxiliary storage 54, a memory device 55, a Central Processing Unit (CPU) 56 and a network connecting device 57 that are connected with each other via a system bus B.

The input device 51 includes a pointing device or the like such as a keyboard, a mouse or the like operated by the user or the like, for example, and inputs various operation signals such as executing the program or the like by the user or the like.

The output device 52 includes a display for displaying a Graphical User Interface (GUI) necessary for operating the computer that executes the processes of the embodiment, screens generated by the screen generating unit 49 or the like, and displays the executed process or result of the program by the control program of the CPU 56.

The input device 51 and the output device 52 may be an integrated input output device such as a touch panel or the like.

The application operation evaluating program that is installed in the computer body is provided by a portable recording medium 58 or the like such as a USB memory, a CD-ROM or the like, for example. The recording medium 58 is capable of being set in the drive device 53 and the program stored in the recording medium 58 is installed in the auxiliary storage 54 via the drive device 53 from the recording medium 58.

The auxiliary storage 54 is a storage such as a hard disk or the like and stores the application operation evaluating program, a control program or the like of the computer, and the data can be input and output in accordance with necessity.

The memory device 55 stores a program or the like that is read out from the auxiliary storage 54 by the CPU 56. For the memory device 55, a Read Only Memory (ROM), a Random Access Memory (RAM) or the like may be used.

The CPU 56 controls entire processes of the computer such as various calculations, input/output of data between each hardware structure unit, or the like, based on a control program such as an Operating System (OS) or the like, and a program stored in the memory device 55. Various information or the like used in executing the programs are obtained from the auxiliary storage 54 and executed results or the like are stored in the auxiliary storage 54.

The network connecting device 57 obtains a program from an external apparatus connected to a communication network or provides an executed result or the like obtained by executing the program to the external apparatus, by connecting to the communication network or the like.

The application operation evaluating apparatus 10 is capable of performing the processes of the embodiment by the above configuration of the hardware structure.

(Application Operation Evaluating Method)

Figure 4:
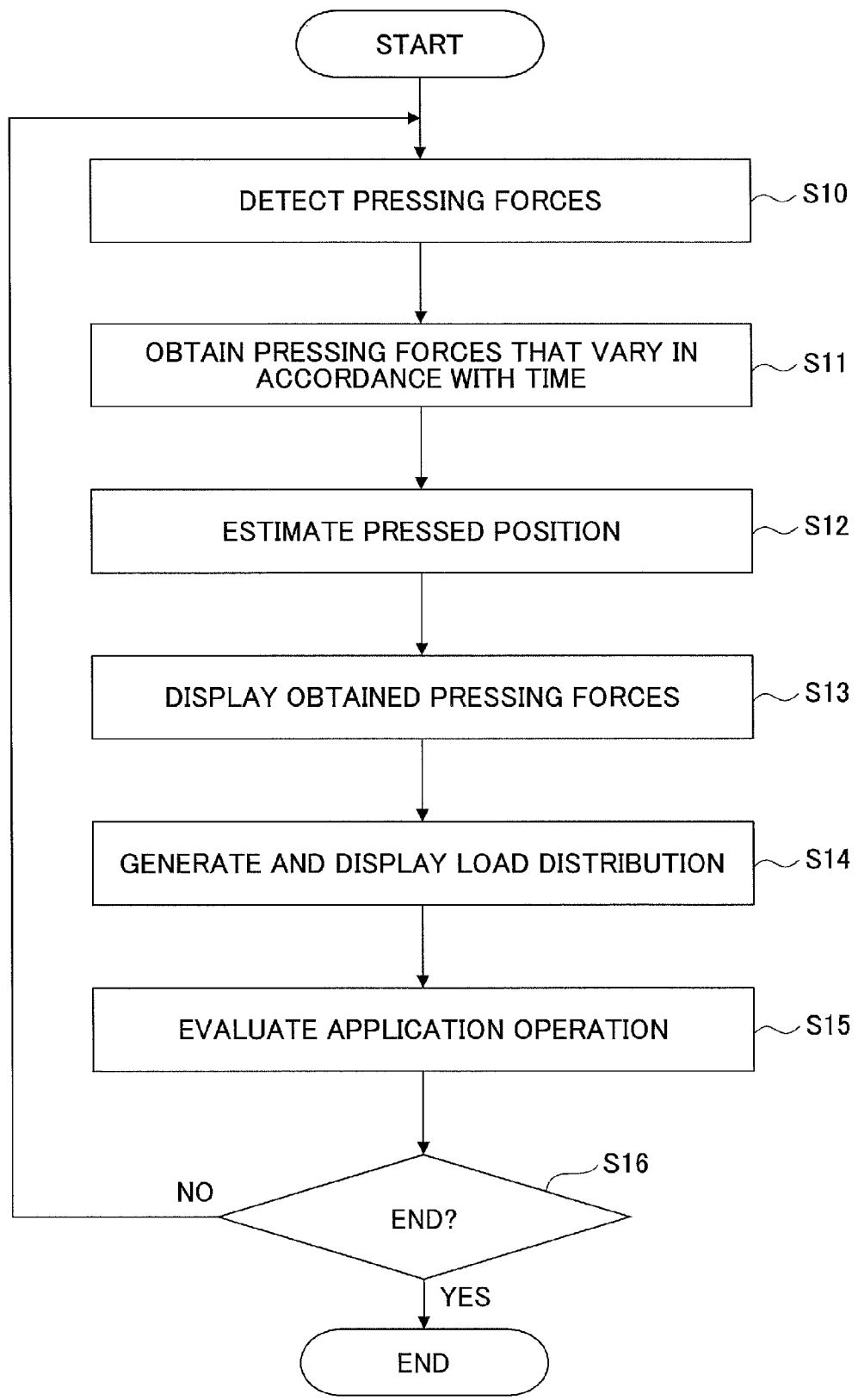
FIG. 4 is a flowchart illustrating an application operation evaluating method of the embodiment.

Next, an application operation evaluating method performed by the application operation evaluating apparatus 10 is explained. FIG. 4 is a flowchart illustrating the application operation evaluating method of the embodiment.

As illustrated in FIG. 4, in the application operation evaluating apparatus 10, when the detecting unit 44 detects the pressing forces obtained front the sensors 22A to 22D in accordance with the application operation to the application target surface 24 (S10), the calculating unit 45 obtains the pressing forces that vary in accordance with time (S11).

The estimating unit 46 estimates the pressed position of the application operation on the application target surface 24 based on the pressing forces each applied to the sensors 22, obtained by the detecting unit 44 (S12).

Next, the output unit 42 displays the pressing forces obtained by the calculating unit 45 (S13). The load distribution generating unit 47 generates the load distribution in accordance with the application operation based on the pressing forces obtained by the detecting unit 44 and the pressed position obtained by the estimating unit 46, and displays the generated load distribution by the output unit 42 (S14).

The evaluating unit 48 compares the peak value of the pressing forces within the predetermined time obtained by the calculating unit 45 with the previously set appropriate value, and evaluates the application operation based on the compared result (S15).

Next, the control unit 50 determines whether the application, operation is finished (S16), and returns to the process of S10 when it is determined that the application operation is not finished (NO in S16). On the other hand, when it is determined that the application operation is finished (YES in S16), the processes are finished.

(Sample Application Method)

Figure 5:
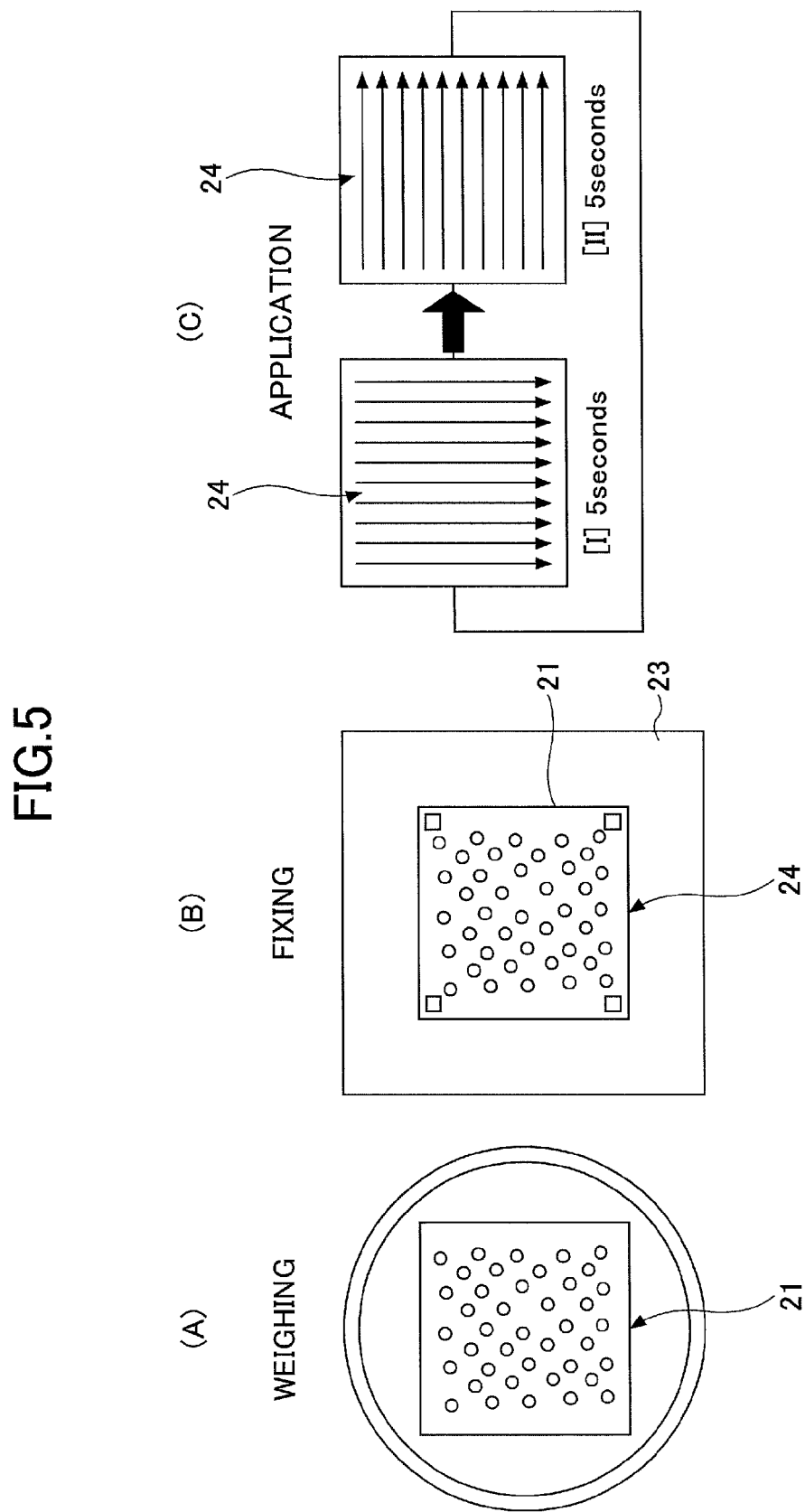
FIG. 5 is a view for explaining a sample application method applied on an application substrate.

Next, a sample application method of applying the sample on the application substrate 21 (steps from sample weighing to application) is explained. FIG. 5 is a view for explaining the sample application method of applying the sample on the application substrate. In FIG. 5, (A) illustrates sample weighing, (B) illustrates fixing the application substrate 21 after sample weighing, and (C) illustrates a flow of application steps.

As illustrated in (A) of FIG. 5, the sample weighing is performed within a range of about 30 to 60 spots on the application substrate 21 with a size of 5×5 cm, for example, using a syringe or the like, for example, within a predetermined time.

Next, as illustrated in (B) of FIG. 5, the application substrate 21 is placed on the sensor unit 20 of the application operation evaluating apparatus 10 and the position of the application substrate 21 is regulated by the position regulating member 23.

Next, the following application operation is started using a finger or a finger cot. First, in step 1, the sample is spread by drawing small circles on the application substrate 21 many times for about 10 seconds. At this time, the sample may be applied on the entirety of the application target surface 24 of the application substrate 21 as spreading by application force of 25 to 50 g.

Next, in step 2, as illustrated in (C) [I] of FIG. 5, an operation of 1 stroke (about 0.5 seconds, for example) in a vertical direction (a longitudinal direction in FIG. 5) is repeated 10 times as an application operation in the vertical direction. Further, as illustrated in (C) [II] of FIG. 5, an operation of 1 stroke (about 0.5 seconds, for example) in a horizontal direction (a lateral direction in FIG. 5) is repeated 10 times as an application operation in the horizontal direction. In step 2, a set of application operation including the application operation in the vertical direction (about 5 seconds, for example) and the application operation in the horizontal direction (about 5 seconds, for example) is repeated 5 times (about 50 seconds, for example).

In this embodiment, the application operation is evaluated based on the application force or the like in accordance with the application operation is evaluated by the application operation evaluating apparatus 10.

(Sensor Calibration in Pressing Force Measurement)

Figure 6:
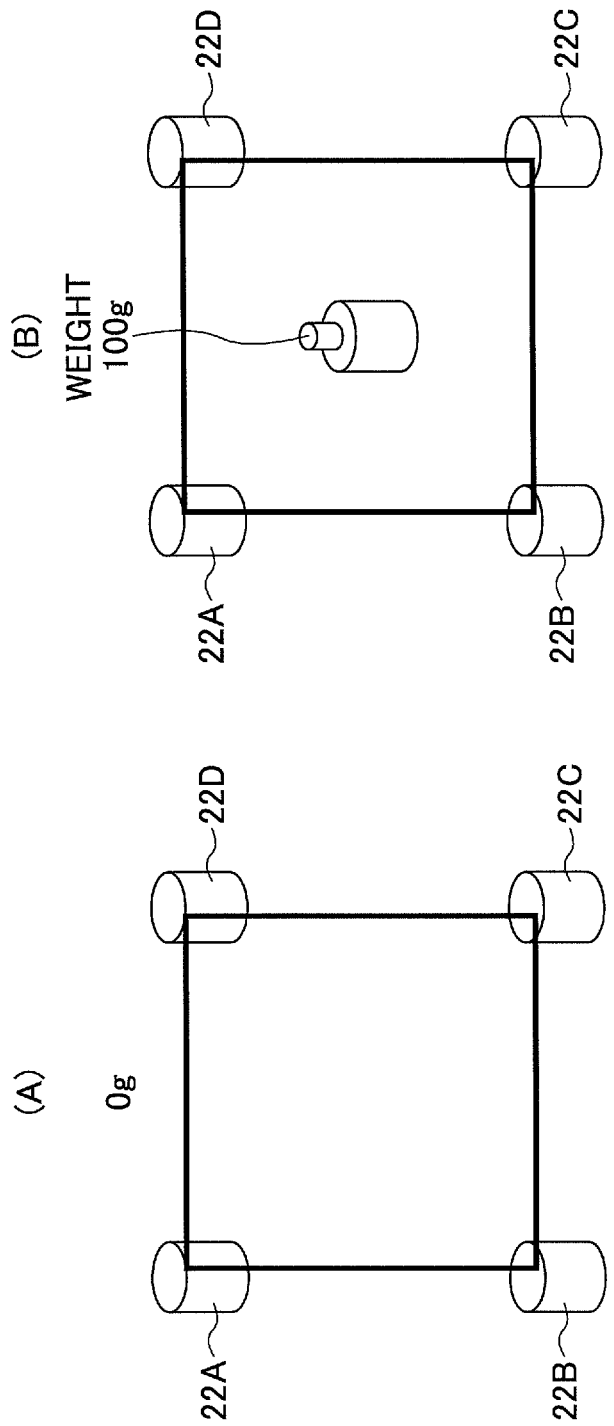
FIG. 6 is a view for explaining sensor calibration in measuring pressing forces.

FIG. 6 is a view for explaining the sensor calibration when measuring the pressing forces. First, the calculating unit 45 performs the following steps as an initial calibration.

As illustrated in (A) of FIG. 6, data (zero value data) of the sensors (sensors 22A to 22D) when nothing is placed (0 g) is obtained as a total output value A. Further, as illustrated in (B) of FIG. 6, data of the sensors (sensors 22A to 22D) when a weight of 100 g, for example, is placed at the center of the application substrate 21 is obtained as a total output value B. The total output value A and the total output value B are calculated from the following equations (1) and (2).

[No. 1]

$$A = \sum_{n=1}^{4} a_{0,n} \quad (1)$$

$$B = \sum_{n=1}^{4} b_{100,n} \quad (2)$$

Here, zero value data $a_{0,n}$ is assumed as each sensor output for 0 g ("n" corresponds to a sensor number 1, 2, 3 and 4, and the numbers 1 to 4 corresponds to the sensors 22A to 22D) and data $b_{100,n}$ is assumed as each sensor output for 100 g. Next, the coefficient k for calibration is obtained. The coefficient k can be obtained from k=100.0/(B-A).

Next, upon starting the measurement, after obtaining the total output value A based on the sensor outputs for 0 g, when an actual measurement is started, data of each sensor is sequentially obtained to calculate a total output value C. Here, each sensor output is assumed as $c_{cal,n}$, and the total output value C is calculated from the following equation (3).

[No. 2]

$$C = \sum_{n=1}^{4} C_{cal,n} \quad (3)$$

Next, measurement pressing force (in other words, pressing force) G is obtained by sequentially calculating a difference between the obtained outputs of the sensors 22 and the sensor outputs for 0 g, and multiplying the coefficient k. The measurement pressing force G can be obtained from G=k(C-A), for example.

(Sensor Calibration before Estimating Pressed Position (Preprocessing))

Figure 7:
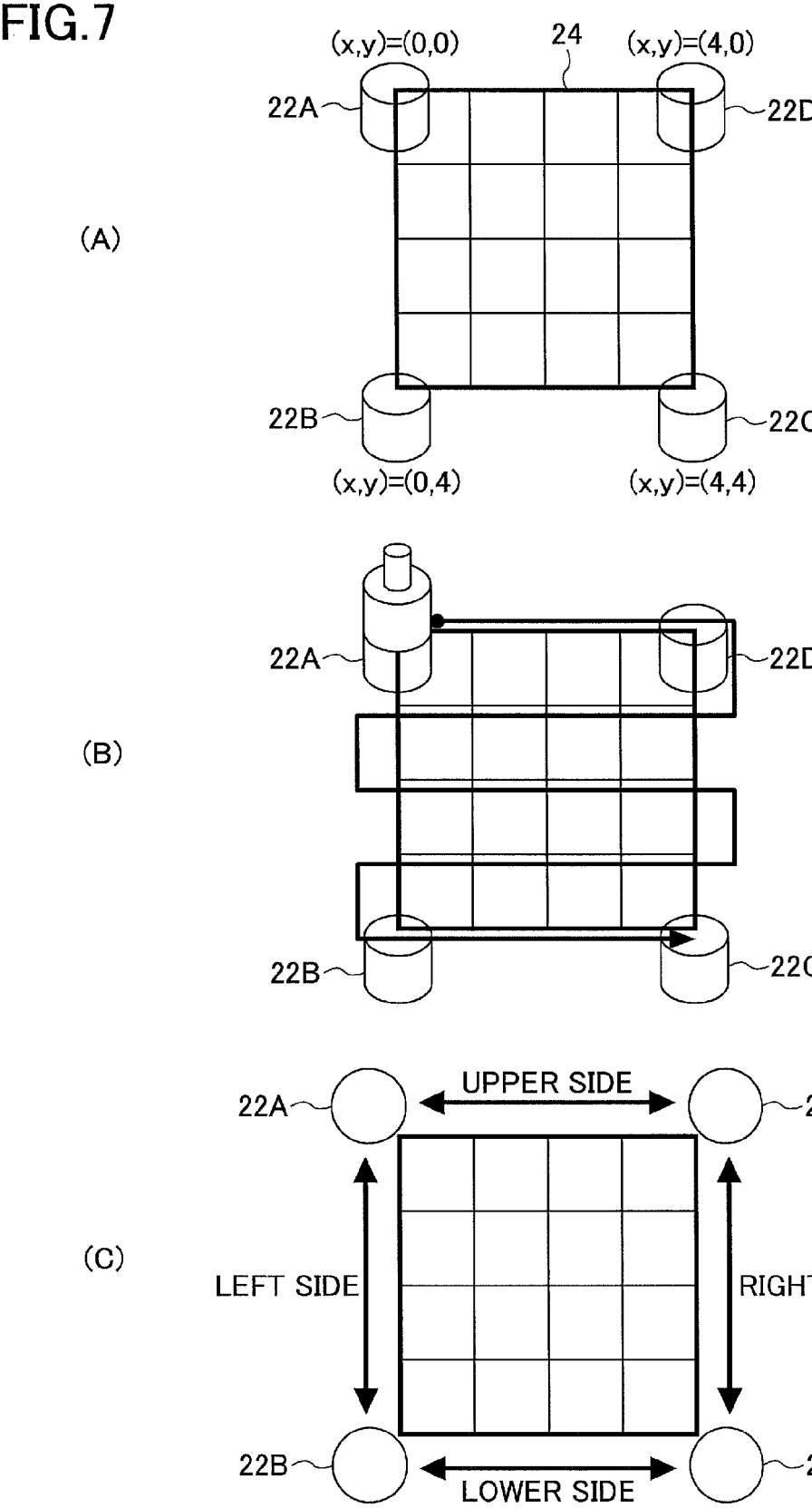
FIG. 7 is a view for explaining the sensor calibration before estimating a pressed position.

FIG. 7 is a view for explaining the sensor calibration before estimating the pressed position. As illustrated in (A) of FIG. 7, a rectangular area of the application target surface 24 provided above the sensors 22A to 22D is divided into 16 areas, and coordinate (x,y) of each of the divided rectangular areas is defined as (x,y)=(0,0) to (4,4).

First, the estimating unit 46 obtains output values (zero value data $a_{0,n}$) obtained from the sensors 22A to 22D when nothing is placed (0 g, for example) on the application target surface 24. Next, by placing a predetermined weight (100 g, for example) at each coordinate point (25 points for the example in (B) of FIG. 7) as illustrated in (B) of FIG. 7, the estimating unit 46 obtains output values $c_{cal,n}$ (x, y) obtained from the sensors 22A to 22D (x=0, 1, 2, 3, 4, y=0, 1, 2, 3, 4).

Next, output values $d_{cal,n}$ (x, y) for each of which the zero value calibration is performed is obtained by subtracting the zero value data $a_{0,n}$ from the output values $c_{cal,n}$ (x, y) when the predetermined weight is mounted. The output values $d_{cal,n}$ (x, y) for each of which the zero value calibration is performed are obtained by the following equation (4). [No. 3]

$$d_{cal,n}(x,y) = c_{cal,n}(x,y) - a_{0,n} \quad (4)$$

Next, total output values $D_{cal,n}$ (x, y) are calculated from the following equation (5), for example, by calculating a total of the output values $d_{cal,n}$ (x, y) for each of which the zero value calibration is performed for the sensors 22A to 22D, at each coordinate point. Further, a ratio (individual output ratio $e_{cal,n}$ (x, y)) of the output value $d_{cal,n}$ (x, y) of each of the sensors 22A to 22D with respect to the total output value $D_{cal,n}$ (x,y) is obtained by the following equation (6).

Here, a calibration value $Val_{cal,n}$ (x, y) is obtained using the following equation (7), for example, such that a difference between the maximum value and the minimum, value of the individual, output ratios $e_{cal,n}$ (x, y) of the sensors 22A to 22D becomes a predetermined value ("100", for example). Next, calibrated values $f_{cal,n}$ (x,y) are obtained by the following equation (8), using the calibration value $Val_{cal,n}$ (x, y), such that the maximum value and the minimum value of the individual output ratios $e_{cal,n}$ (x, y) of the sensors 22A to 22D become the predetermined values ("100" and "0", for example).

[No. 4]

$$D_{cal}(x, y) = \sum_{n=1}^{4} d_{cal,n}(x, y) \quad (5)$$

$$e_{cal,n}(x, y) = d_{cal,n}(x, y) / D_{cal}(x, y) \quad (6)$$

$$Val_{cal,n} = 100 / \max\{e_{cal,n}(x, y)\} - \min\{e_{cal,n}(x, y)\} \quad (7)$$

$$f_{cal,n}(x, y) = (e_{cal,n}(x, y) - \min\{e_{cal,n}(x, y)\}) \times Val_{cal,n} \quad (8)$$

As described above, the sensor calibration is previously performed. Further, as will be explained in the following, coordinate correction amounts for setting coordinates of a rectangular area (a calibration target area) of the application target surface 24 are obtained using the calibrated values $f_{cal,n}$ (x, y).

As illustrated in (C) of FIG. 7, a side including the sensor 22A and the sensor 22B at an end portion is referred to as a "left side" and a side including the sensor 22B and the sensor 22C as an end portion is referred to as a "lower side". Further, a side including the sensor 22C and the sensor 22D as an end portion is referred to as a "right side" and a side including the sensor 22D and the sensor 22A is referred to as an "upper side". Further, it is explained that a rectangular area (in other words, a calibration target area) surrounded by those sides corresponds to the application target surface 24.

(Flow of Obtaining Steps of Coordinate Correction Amount)

Figure 8:
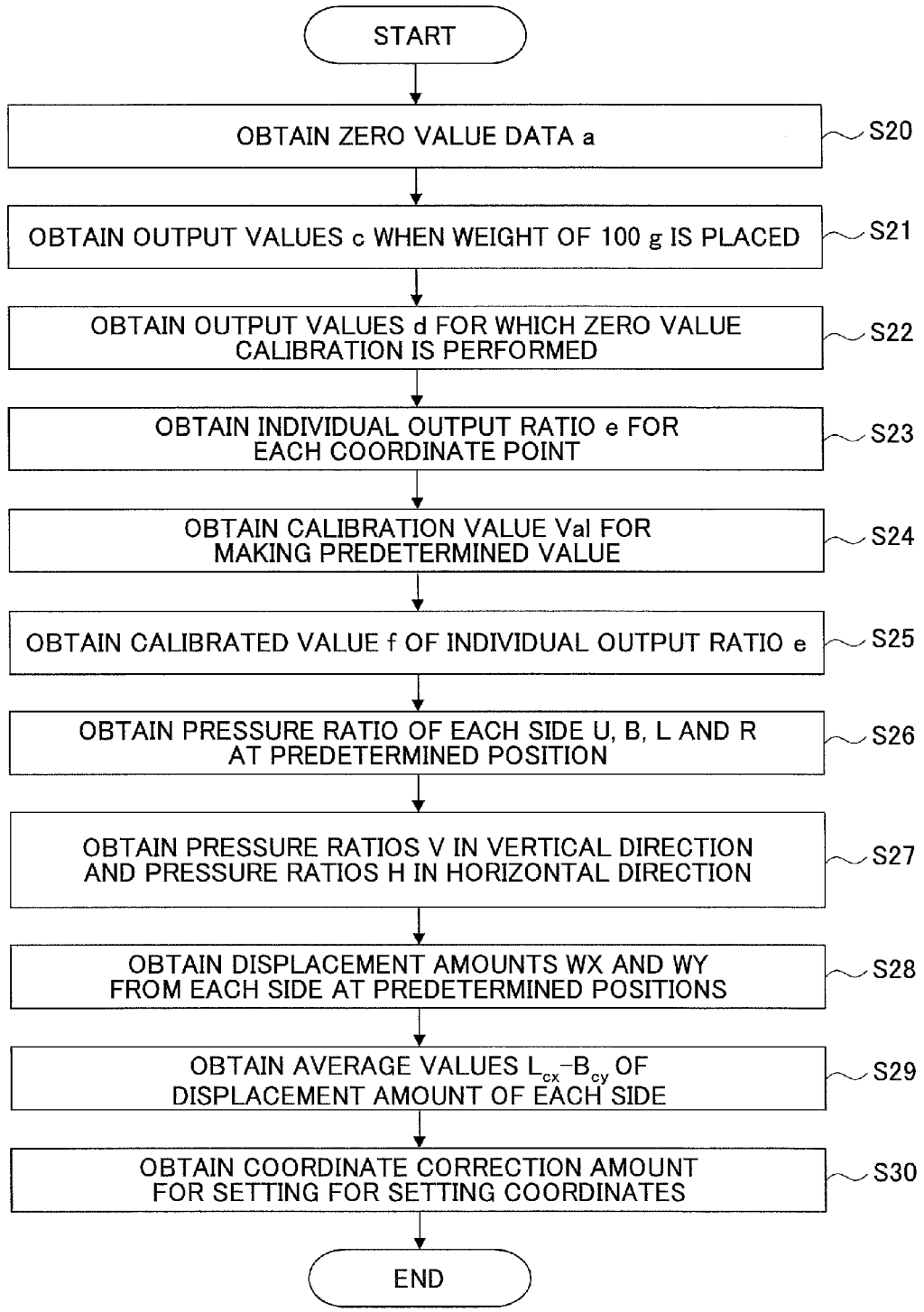
FIG. 8 is a flowchart illustrating a flow of a coordinate correction amount obtaining process.

FIG. 8 is a flowchart illustrating a flow of obtaining steps of a coordinate correction amount. As illustrated in FIG. 8, when the zero value data $a_{0,n}$ is obtained from the sensors 22A to 220 (S20), the output values $c_{cal,n}$ (x, y) in a case when the predetermined weight (100 g, for example) is placed at each coordinate point (25 points for the example in (C) of FIG. 7) are obtained (S21). Then, the output values $d_{cal,n}$ (x, y) are obtained for each of which the zero value calibration is performed at each coordinate point (S22).

Next, when the total output value $D_{cal,n}$ (x, y) of each coordinate point is obtained, the ratio (individual output ratio $e_{cal,n}$ (x, y)) of the output values $d_{cal,n}$ (x, y) of each of the sensors 22A to 22D with respect to the total output value $D_{cal,n}$ (x, y) is obtained for each coordinate point (S23).

Next, the maximum value and the minimum value of the individual output ratios $e_{cal,n}$ (x, y) of the sensors 22A to 22D are obtained. Then, the calibration value $Val_{cal,n}$ is obtained by which a difference between the obtained maximum value and the minimum value becomes a predetermined value (100, for example) (S24).

Next, the individual output ratios $e_{cal,n}$ (x, y) are corrected using the calibration value $V_{cal,n}$ (x, y) such that the maximum value and the minimum value of the sensors 22A to 22D become predetermined values (100 and 0, for example), respectively, to obtain the calibrated values $f_{cal,n}$ (x,y) (S25).

Next, pressure ratios to the sides $U_{cal}$ (x,y), $B_{cal}$ (x, y), $L_{cal}$ (x,y) and $R_{cal}$ (x,y) at each of a predetermined positions (16 points that contact an outer periphery of the application target surface 24 among the above described 25 points, for example) with respect to each side are obtained using the following equation (9) (S26).

[No. 5]

$$U_{cal}(x,y) = f_{cal,4}(x,y)/(f_{cal,1}(x,y) + f_{cal,4}(x,y))$$

$$B_{cal}(x,y) = f_{cal,3}(x,y)/(f_{cal,2}(x,y) + f_{cal,3}(x,y))$$

$$L_{cal}(x,y) = f_{cal,2}(x,y)/(f_{cal,1}(x,y) + f_{cal,2}(x,y))$$

$$R_{cal}(x,y) = f_{cal,3}(x,y)/(f_{cal,3}(x,y) + f_{cal,4}(x,y)) \quad (9)$$

For example, in order to obtain the pressure ratio at coordinate (0,0) with respect to the upper side, $U_{cal}$ (0,0)=$f_{cal,4}$ (0,0)/($f_{cal,1}$ (0,0)+$f_{cal,4}$ (0,0)) is used. Similarly, the pressure ratios at coordinate (0,0) with respect to the lower side, the left side and the right side are respectively obtained.

Next, the pressure ratio $V_{cal}$ (x,y) in the vertical direction or the pressure ratio $H_{cal}$ (x,y) in the horizontal direction when each of the above described predetermined positions (16 points that contact an outer periphery of the application target surface 24 among the above described 25 points, for example) is pressed is obtained using the following equation (10) (S27).

[No. 6]

$$V_{cal}(x,y) = (f_{cal,1}(x,y) + f_{cal,4}(x,y))/(f_{cal,1}(x,y) + f_{cal,2}(x,y) + f_{cal,3}(x,y) + f_{cal,4}(x,y))$$

$$H_{cal}(x,y) = (f_{cal,1}(x,y) + f_{cal,2}(x,y))/(f_{cal,1}(x,y) + f_{cal,2}(x,y) + f_{cal,3}(x,y) + f_{cal,4}(x,y)) \quad (10)$$

Next, displacement amounts $WX_{cal}$ (x,y) and $W_{cal}$ (x,y) from each side at each of the above described predetermined positions (16 points that contact an outer periphery of the application target surface 24 among the above described 25 points, for example) are obtained using the following equation (11) (S28).

A method of obtaining the equation used in obtaining displacement amounts $WX_{cal}$ (x,y) and $WY_{cal}$ (x, y) from each side is explained later. The displacement amounts are converted to positional information corresponding to output values of the sensors 22A to 22D when a predetermined position is pressed.

[No. 7]

$$WX_{cal}(x,y)=(U_{cal}(x,y)\times(1-V_{cal}(x,y))30\,B_{cal}(x,y)\times V_{cal}(x,y))$$

$$WY_{cal}(x,y)=(L_{cal}(x,y)\times(1-H_{cal}(x,y))30\,R_{cal}(x,y)\times H_{cal}(x,y)) \quad (11)$$

Next, an average value of the displacement amounts of the above described each side is obtained using the following equation (12) (S29).

[No. 8]

$$\text{LEFT SIDE: } L_{CX} = \text{average}(WX_{cal}(0,y)) \quad (12)$$
$$\text{RIGHT SIDE: } R_{CX} = \text{average}(WX_{cal}(4,y))$$
$$y = 0, 1, 2, \ldots, 4$$
$$\text{UPPER SIDE: } U_{Cy} = \text{average}(WY_{cal}(x,0))$$
$$\text{LOWER SIDE: } B_{Cy} = \text{average}(WY_{cal}(x,4))$$
$$x = 0, 1, 2, \ldots, 4$$

For example, for a case of the left side, an average value of the displacement amount of the left side is obtained from displacement amounts obtained for coordinate points (0,1), (0,2), (0,3) and (0,4) of the left side ($L_{CX}$=average ($WX_{cal}(0,y)$). Similarly, average values of the displacement amounts of the right side, the upper side and the lower side are obtained from displacement amounts obtained for coordinate points of the right side, the upper side and the lower side, respectively.

Next, a coordinate correction amount for setting coordinates of the rectangular area (in other words, calibration target area) of the application target surface 24 is obtained (S30), and the processes are finished.

Here, for example, it is assumed that the average value Lcx of the displacement amount of the left side is assumed as a reference point calXval, and the average value Ucy of the displacement amount of the upper side is assumed as a reference point calYval. Further, by using a difference between the average value Lcx of the displacement amounts of the left side and the average value Rcx of the displacement amounts of the right side, resolution calXscale by which the difference becomes a predetermined value (100, for example) is obtained. Similarly, by using a difference between the average value Ucy of the displacement amounts of the upper side and the average value Bcy of the displacement amounts of the lower side, resolution calYscale by which the difference becomes a predetermined value (100, for example) is obtained.

Here, the above described coordinate correction amounts (reference points calXval and calYval, and resolutions calXscale and calYscale) are obtained using the following equation (13), for example.

[No. 9]

$$\text{calXval}=L_{CX}$$

$$\text{calYval}=U_{Cy}$$

$$\text{calXscale}=100/(R_{CX}-L_{CX})$$

$$\text{calYscale}=100/(B_{Cy}-U_{Cy}) \quad (13)$$

As described above, it is assumed that the coordinate correction amounts for setting the coordinate of the calibration target area are previously obtained and used in the pressed position estimating process. However, an example of obtaining the coordinate correction amounts is not limited so.

(Method of Obtaining Equation that is used in Obtaining Displacement Amount)

Figure 9:
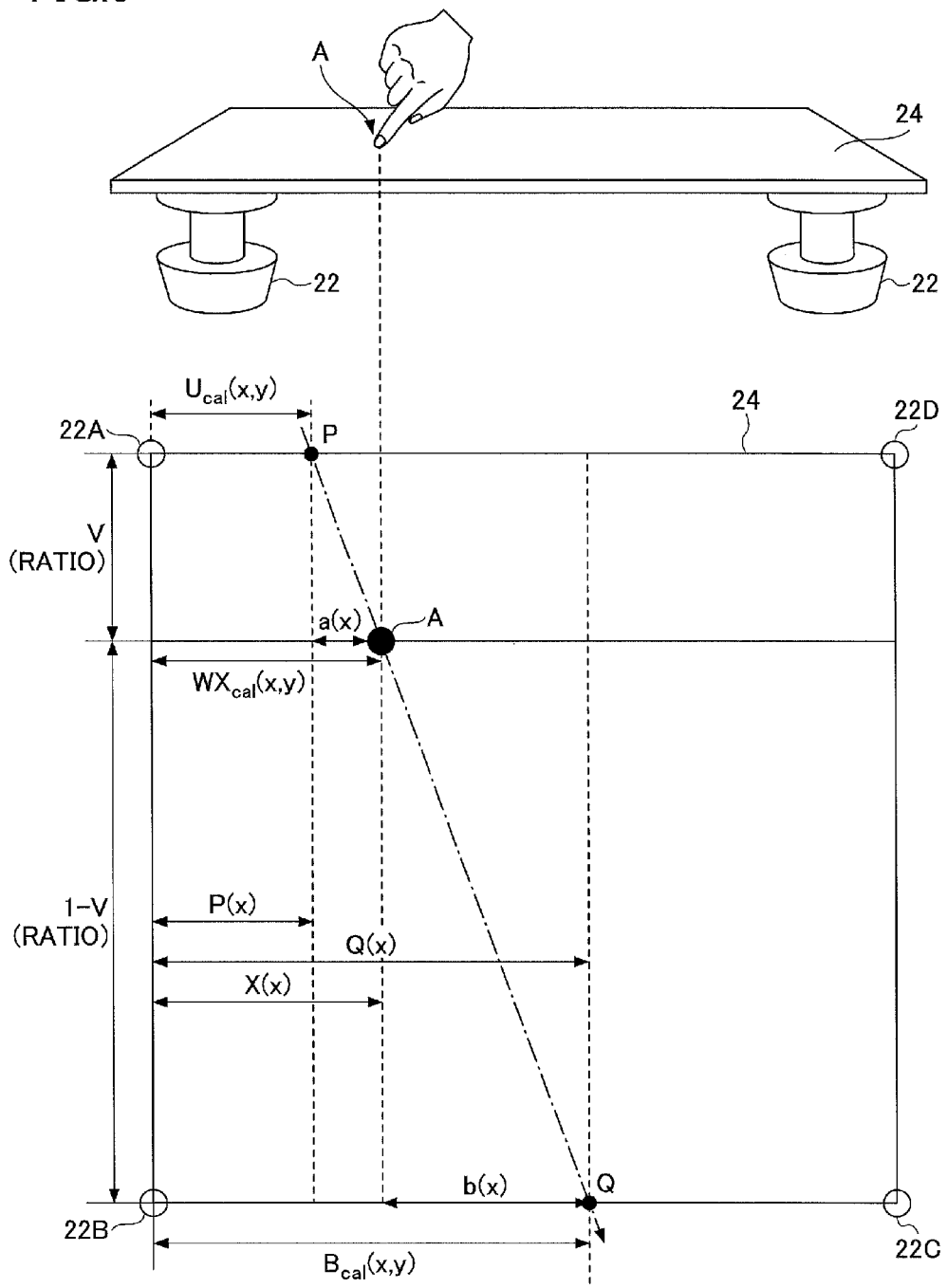
FIG. 9 is a view for explaining an example of obtaining an equation that is used in obtaining the displacement amounts.

Next, the above described equation (11) used in obtaining the displacement amounts is explained. FIG. 9 is a view for explaining an example of obtaining an equation that used in obtaining the displacement amounts.

As illustrated in FIG. 9, a method of obtaining the displacement amount WX (in other words, X coordinate) at a pressed position, when an arbitrary position (a pressed position A, for example) of the application target surface 24 is pressed, from each side is explained. Here, a ratio of load ratios of the upper side and the lower side in the X direction (lateral direction) is added, for example.

As described above, the pressure ratio of the upper side is expressed as follows.

$$U_{cal}=f_{cal,4}/(f_{cal,1}+f_{cal,4})$$

The pressure ratio of the lower side is expressed as follows.

$$B_{cal}=f_{cal,3}/(f_{cal,2}+f_{cal,3})$$

Then, for example, the weight ratio of the upper side with respect to a total and the weight ratio of the lower side with respect to the total are expressed as follows.

For example, it is assumed that the weight ratio of the upper side with respect to the total is expressed as follows.

$$V_{cal}=(f_{cal,1}+f_{cal,4})/(f_{cal,1}+f_{cal,2}+f_{cal,3}+f_{cal,4})$$

Assuming that the total of the weight ratios of the upper side and the lower side is "1", the weight ratio of the lower side can foe expressed as follows.

$$1-V_{cal}=(f_{cal,2}+f_{cal,3})/(f_{cal,1}+f_{cal,2}+f_{cal,3}+f_{cal,4})$$

Here, $V_{cal}$ is an equation same as the one explained above as the pressure ratio in the vertical direction.

Here, when the pressed position A is pressed, it is assumed that pressure at a point P ($U_{cal}$,0) of the upper side is $f_{cal,1}+f_{cal,4}$ and pressure at a point Q ($B_{cal}$,0) of the lower side is $f_{cal,2}+f_{cal,3}$.

The X coordinate (in other words, x coordinate of WX) of barycenter of the point P and the point Q can be expressed as follows. For example, it is assumed that there are masses m and n and it is assumed that coordinates of mass points a and b are (Xa,Ya) and (Xb,Yb), respectively. In this case, equations for obtaining coordinate (X,Y) of barycenter of the mass points a and b (in other words, an equation that internally divides the mass point a with the mass m and the mass point b with the mass n) become as follows.

$$X=(n\times Xa+m\times Xb)/(m+n)$$

$$Y=(n\times Ya+m\times Yb)/(m+n)$$

According to the above equations, the following equation can be obtained.

$$WX(x) = (U_{cal}\times(f_{cal,2}+f_{cal,3})+B_{cal}\times(f_{cal,1}+f_{cal,4}))/ \quad (14)$$
$$(f_{cal,2}+f_{cal,3}+f_{cal,1}+f_{cal,4})$$
$$= U_{cal}\times(f_{cal,2}+f_{cal,3})/(f_{cal,2}+f_{cal,3}+f_{cal,1}+f_{cal,4}) +$$
$$B_{cal}\times(f_{cal,1}+f_{cal,4})/(f_{cal,2}+f_{cal,3}+f_{cal,1}+f_{cal,4})$$
$$= (U_{cal}\times(1-V_{cal})+B_{cal}\times V_{cal})$$

Similarly, when the pressed position A is pressed, the y coordinate of the displacement WX can be expressed as follows.

$$WX(y) = (0 \times (f_{cal,2} + f_{cal,3}) + 1 \times (f_{cal,1} + f_{cal,4}))/$$
$$(f_{cal,2} + f_{cal,3} + f_{cal,1} + f_{cal,4})$$
$$= f_{cal,1} + f_{cal,4}/(f_{cal,2} + f_{cal,3} + f_{cal,1} + f_{cal,4})$$
$$= V_{cal}$$

WX(x,y) can be expressed as follows based on the above described WX(x) and WX(y),.

$$WX(x,y) = (U_{cal} \times (1-V_{cal}) + B_{cal} \times V_{cal}, V_{cal})$$

Thus, the X coordinate of the pressed position A to which load ratios of the upper side and the lower side in the lateral direction are added can be expressed as $U_{cal} \times (1-V_{cal}) + B_{cal} \times V_{cal}$.

Further, a method of obtaining the displacement amount WY (in other words, Y coordinate) at the pressed position A, when the pressed position A is pressed, from each side is explained. Here, a ratio of load ratios of the right side and the left side in the Y direction (longitudinal direction) is added, for example.

As described above, it is assumed that the pressure ratio of the left side is expressed as follows.

$$L_{cal} = f_{cal,2}/(f_{cal,1} + f_{cal,2})$$

The pressure ratio of the right side is expressed as follows.

$$R_{cal} = f_{cal,2}/(f_{cal,3} + f_{cal,4})$$

Here, it is assumed that the weight ratio of the left side to the total and the weight ratio of the right side to the total are expressed as follows.

For example, it is assumed that the weight ratio of the left side total is expressed as follows.

$$H_{cal} = (f_{cal,1} + f_{cal,2})/(f_{cal,1} + f_{cal,2} + f_{cal,3} + f_{cal,4})$$

Assuming that the total of the weight ratios of the left side and the right side is "1", the weight ratio of the right side can foe expressed as follows.

$$H_{cal} = (f_{cal,3} + f_{cal,4})/(f_{cal,1} + f_{cal,2} + f_{cal,3} + f_{cal,4})$$

Here, $H_{cal}$ is an equation same as the one explained above as the pressure ratio in the horizontal direction.

Here, when the pressed position A is pressed, it is assumed that the pressure of the point P'(0, $L_{cal}$) at the left side is assumed as $f_{cal,1} + f_{cal,2}$ and the pressure at the point Q' (1,$R_{cal}$) at the right side is assumed as $f_{cal,3} + f_{cal,4}$.

The Y coordinate (in other words, the y coordinate of WY) of the barycenter of the point P' and the point Q' can be expressed as follows by the above described equation that internally divides the mass point a of the mass m and the mass point b of the mass n.

$$WY(y) = (L_{cal} \times (f_{cal,3} + f_{cal,4}) + R_{cal} \times (f_{cal,1} + f_{cal,2}))/$$
$$(f_{cal,3} + f_{cal,4} + f_{cal,1} + f_{cal,2})$$
$$= L_{cal} \times (f_{cal,3} + f_{cal,4})/(f_{cal,3} + f_{cal,4} + f_{cal,1} + f_{cal,2}) +$$
$$R_{cal} \times (f_{cal,1} + f_{cal,2})/(f_{cal,3} + f_{cal,4} + f_{cal,1} + f_{cal,2})$$
$$= (L_{cal} \times (1 - H_{cal}) + R_{cal} \times H_{cal})$$

Similarly, when the pressed position A is expressed, the x coordinate of the displacement amount WY can be expressed as follows.

$$WY(x) = (0 \times (f_{cal,3} + f_{cal,4}) + 1 \times (f_{cal,1} + f_{cal,2}))/$$
$$(f_{cal,3} + f_{cal,4} + f_{cal,1} + f_{cal,2})$$
$$= f_{cal,1} + f_{cal,2}/(f_{cal,3} + f_{cal,4} + f_{cal,1} + f_{cal,2})$$
$$= H_{cal}$$

WY(x,y) can be expressed as follows based on the above described WY(x) and WY(y).

$$WY(x,y) = (H_{cal}, L_{cal} \times (1-H_{cal}) + R_{cal} \times H_{cal})$$

Thus, the Y coordinate of the pressed position A to which load ratios of the left side and the right side in the longitudinal direction are added can be expressed as $L_{cal} \times (1-H_{cal}) + R_{cal} \times H_{cal}$.

The above described WX and WY may be obtained as follows.

For example, for WX, it is assumed that the left end of the upper side is coordinate (x1,y1), the left end of the lower side is coordinate (x1,y1,+1), the right end of the upper side is coordinate (x4,y4) and the right end of the lower side is coordinate (x4, y4+1) in FIG. 9.

Further, it is assumed that the coordinate of the point P is (Px,Py), the pressure ratio from the coordinate (x1,y1) of the upper side to the point P is $f_{cal,1}/(f_{cal,1}+f_{cal,4})$ and the pressure ratio from the point P to the coordinate (x4,y4) of the upper side is $f_{cal,4}/(f_{cal,1}+f_{cal,4})$.

Further, it is assumed that the coordinate of the above described point Q is (Qx,Qy), the pressure ratio from the coordinate (x1,y1+1) of the lower side to the point Q is $f_{cal,2}/(f_{cal,2}+f_{cal,3})$ and the pressure ratio from the point Q to the coordinate (x4,y4+1) of the lower side is $f_{cal,3}/(f_{cal,2}+f_{cal,3})$.

At this time, Px and Qx can be expressed as follows.

$$Px = x1 + (x4-x1) \times f_{cal,1}/(f_{cal,1}+f_{cal,4})$$

$$Qx = x1 + (x4-x1) \times f_{cal,2}/(f_{cal,2}+f_{cal,3})$$

Thus, WX can be expressed as follows.

$$WX = Px \times (f_{cal,2} + f_{cal,3})/(f_{cal,1} + f_{cal,2} + f_{cal,3} + f_{cal,4}) + \quad (15)$$
$$Qx \times (f_{cal,1} + f_{cal,4})/(f_{cal,1} + f_{cal,2} + f_{cal,3} + f_{cal,4})$$
$$= Px \times (1 - V) + Qx \times V$$

As the equation (15) has the same meaning as the above described equation (14), WX can be obtained by the above described method. For a case of WY, WY can be obtained by the similar method as that of WX.

(Another Example of Obtaining Equation that is used in Obtaining Displacement Amount)

Further, another method of obtaining the equation (11) that is used in obtaining the above described displacement amount is explained. For example, it is assumed that, in an example of FIG. 9, an amount from the left side to the point P is P(x), an amount from the left side to the point Q is Q(x) and an amount from the left side to the pressed position A is X (x).

Further, it is assumed that an amount from a crossing point of a line from the point P toward the lower side in a perpendicular direction with respect to the lower side and a line from the left side toward the right side in a perpendicular direction with respect to the left side and the right side that passes the pressed position A, to the pressed position A is a(x). Further, it is assumed that an amount from a crossing point of a line from the upper side to the lower side in a perpendicular direction with respect to the upper side and the lower side that passes the pressed position A and the lower side, to the point Q is b(x).

At this time, the X coordinate of the pressed position A can be expressed by the following method.

$$\text{When assuming } a(x): V = b(x):(1-V), \quad (16)$$
$$a(x) \times (1-V) = b(x) \times V$$
$$= (Q(x) - P(x) - a(x)) \times V$$
$$= Q(x) \times V - P(x) \times V - a(x) \times V$$

$$a(x) \times (1-V) + a(x) \times V = Q(x) \times V - P(x) \times V$$
$$a(x) - (a(x) \times V) + (a(x) \times V) = Q(x) \times V - P(x) \times V$$
$$a(x) = Q(x) \times V - P(x) \times V.$$

This means,
$$X(x) = P(x) + a(x)$$
$$= P(x) - P(x) \times V + Q(x) \times V$$
$$= P(x) \times (1-V) + Q(x) \times V.$$

Alternatively, $a(x): V = (a(x) + b(x)):1$
$$a(x) = (a(x) \times V) + (b(x) \times V)$$
$$a(x) - (a(x) \times V) = b(x) \times V$$
$$= (Q(x) - P(x) - a(x)) \times V$$
$$= Q(x) \times V - P(x) \times V.$$

This means as follows.
$$X(x) = P(x) + a(x)$$
$$= P(x) - P(x) \times V + Q(x) \times V$$
$$= P(x) \times (1-V) + Q(x) \times V$$

As the equation (16) has the same meaning as the above described equation (14) and the equation (15), WX can be obtained by the above described method. For a case of WY, WY can be obtained by the similar method as that of WX.

By obtaining the displacement amounts WX and WY of the pressed position, when the position is pressed by the user, for example, from each side by using the above described equations for obtaining the displacement amounts, the pressed position can be estimated as follows.

(Flow of Pressed Position Estimating Process)

Figure 10:
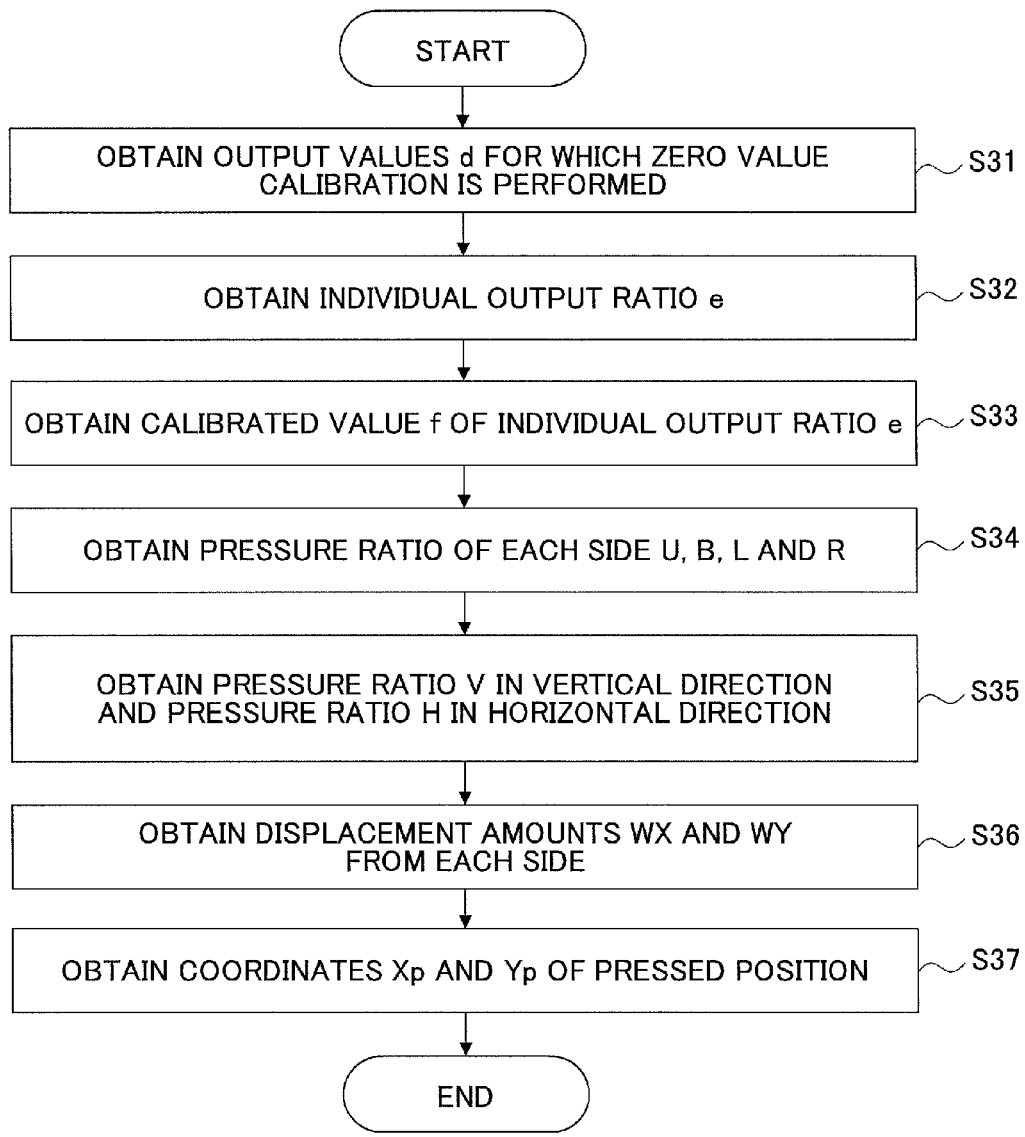
FIG. 10 is a flowchart illustrating a flow of a pressed position estimating process.

Next, a pressed position estimating process when the application target surface 24 (in other words, the calibration target area) is actually pressed by a user is explained. FIG. 10 is a flowchart illustrating a flow of the pressed position estimating process. Steps from S31 to S36 in FIG. 10 are performed by the method similar to the steps from S22 to S23 and S25 to S28 in FIG. 8.

Here, the steps of FIG. 10 are different from those of FIG. 8 in which displacement amounts are obtained when predetermined positions (25 points that are divided by the same interval, for example) are pressed by mounting a predetermined weight at the predetermined positions for setting the coordinates of the application target surface 24, in that the displacement amounts are obtained based on the output values obtained from the sensors 22A to 22D when the user presses.

as illustrated in FIG. 10, when pressing force by the user is detected in the actual measurement, the zero value data a obtained in the step of S20 in FIG. 8 is subtracted from each of the output values from the sensors 22A to 22D to obtain the output values $d_{cal}$ for each of which the zero value calibration is performed (S31).

Next, the total output value $D_{cal}$ is obtained from the four output values $d_{cal}$ obtained in the step of S31 and a ratio of the output value with respect to the total output value $D_{cal}$ (individual output ratio $e_{cal}$) of each of the sensors 22A to 22D is obtained (S32).

Next, the maximum value and the minimum value of the individual output ratios $e_{cal}$ of the sensors 22A to 22D are obtained. Then, the individual output ratios $e_{cal}$ are calibrated by the calibration value $Val_{cal}$ obtained in the step of S24 in FIG. 8 such that the maximum value and the minimum value become the predetermined values (100 and 0, for example), respectively, to obtain the calibrated values $f_{cal}$ (S33).

Next, the pressure ratios $U_{cal}$, $B_{cal}$, $L_{cal}$ and $R_{cal}$ of each side are obtained using the four calibrated values $f_{cal}$ obtained in the step of S33 (S34). Next, the pressure ratio $V_{cal}$ in the vertical direction or the pressure ratio $H_{cal}$ in the horizontal direction is obtained (S35). Next, displacement amounts $WX_{cal}$ and $WY_{cal}$ from each side are obtained (S36).

Next, coordinate Xp,Yp of the pressed position is obtained by correcting the displacement amounts $WX_{cal}$ and $WY_{cal}$ from each side obtained in the step of S36 by the coordinate correction amounts (reference points calXval and calYval, and resolutions calXscale and calYscale, for example) previously obtained in the step illustrated in FIG. 8 (S37), and the processes are finished.

Here, it is assumed that a reference point for coordinates is calXval and calYval, and the displacement amounts $WX_{cal}$ and $WY_{cal}$ corrected by the resolutions calXscale and calYscale are set as a coordinate Xp,Yp of the pressed position. The coordinate Xp,Yp of the pressed position may be obtained by using the following equation (17).

[No. 10]

$$\text{Xp}=(WX_{cal}-\text{calXval}) \times \text{calXscale}$$

$$\text{Yp}=(WY_{cal}-\text{calYval}) \times \text{calYscale} \quad (17)$$

An origin (reference point) of the coordinate Xp,Yp obtained in the step of S37 is, for example, a crossing point of the left side and the lower side of the application target surface 24 (in other words, a corner at left and lower). Thus, for example, in order to make the center of the application target surface 24 an origin, positional offset values calXposOffset and calYposOffset may be obtained using a predetermined value (50 when a diagonal line is divided by 100, for example) to express the coordinate Xp, Yp of the pressed position.

For example, the positional offset values calXposOffset and calYposOffset may be obtained by the following equation (18).

[No. 11]

$$\text{calXposOffset}=50-\text{Xp}$$

$$\text{calYposOffset}=50-\text{Yp} \quad (18)$$

Next, the coordinate Xp,Yp of the pressed position is changed to a value from the a center coordinate (in other words, coordinate Xpos,Ypos) using the positional offset values calXposOffset and calYposOffset. The coordinate Xpos, Ypos may be obtained by the following equation (19), for example.

[No. 12]

$$\text{Xpos}=\text{Xp}+\text{calXposOffset}$$

$$\text{Ypos}=\text{Yp}+\text{calYposOffset} \quad (19)$$

As such, using the coordinate correction amounts for setting coordinates that are previously obtained, the pressed position on the application target surface 24 that is pressed by a user at an actual measurement can be determined.

According to the above described steps, the estimating unit 46 can estimate the pressed position of the application operation on the application target surface 24 based on the pressing forces applied to the sensors 22 obtained by the detecting unit 44, respectively. The method of measuring the pressing forces and the method of estimating the pressed position of the embodiment are not limited so.

(Display Screen of Application Operation Evaluating Apparatus 10)

Next, an example of a screen generated by the screen generating unit 49 and is displayed, by the application operation evaluating apparatus 10 is explained. FIG. 11 is a view illustrating an example of a display screen displayed during the application operation.

A screen 60 illustrated in (A) of FIG. 11 includes a sample display part 61, an operation display part 62, a pressing force transit display part 63, a load distribution display part 64 and an evaluation result display part 65.

In the sample display part 61, a sample name or the like ("Sample A" for the example illustrated in FIG. 7) of a skin lotion input by the input unit 41 is displayed.

In the operation display part 62, selection buttons such as "REC", "PLAY", "LOAD", "RESULT" or the like are displayed. For example, when the "REC" button is pressed before an application operation of the above described step 1 or step 2 is performed, the pressing force and the pressed position detected in accordance with the application operation are stored in the storing unit 43.

Further, when the "PLAY" button is selected, the output unit 42 outputs a starting sound that indicates starting of the application operation, and then outputs an indicating sound for indicating a timing to match the application operation to a speed of each step (1 stroke/0.5 seconds, for example), for example.

In the pressing force transit display part 63, the variance of the pressing force in accordance with time is displayed by a line graph or the like in which the horizontal axis indicates Time (sec) and the vertical axis indicates pressing force (g). The waveform 66 illustrated in (A) of FIG. 11 is a signal of time axis obtained every 20 ms, for example.

In the load distribution display part 64, a screen corresponding to the application target surface 24 is displayed. Specifically, the load distribution generating unit 47 generates load distribution using the accumulated value of the accumulated pressing force for each of the pressed positions estimated by the estimating unit 46. The load distribution generated as such is displayed in the screen corresponding to the application target surface 24.

In the example of (A) of FIG. 11, the color distribution expressed in different colors depending on the strength of the accumulated pressing force (from 20 g expressed by the color 67 to 200 g expressed by the color 68 or the like, for example) is displayed. Using the color distribution, in the load distribution display part 64, a state in which the load is applied is displayed by the color 68 at an area corresponding to a center portion of the application target surface 24 and a state in which the load is not applied is displayed by the color 67 at end portions of the application target surface 24.

By displaying the applied condition of the sample by the above described load distribution, it is possible to grasp the pressed result per point, for example. This means that as a point to which the sample is applied for many times or a point to which the force is applied can be visualized, for example, the point to which unevenness of the sample occurs, the point at which the sample is scraped off can be easily grasped.

Further, a result determined by the evaluating unit 48 whether each peak of the pressing force every one stroke (each 0.5 second, for example) is included within a previously set appropriate value (for the example of (A) of FIG. 11, within a range of 75 g to 125 g that is shaded) is displayed in the evaluation result display part 65 (for the example of (A) of FIG. 11, "Good").

When the "RESULT" button of the operation display part 62 is selected, a screen 69 illustrated in (B) of FIG. 11 is displayed. For the example of (B) of FIG. 11, an average value (Ave-g) of the application force (Finger Pressure) for each previously set step (Step), a value (%) of uniformity of pressure distribution (Uniformity) and the load distribution after the steps are finished are displayed. Further, at a determined result (Total Judgment), acceptance (or failure) is determined based on whether the values of the average value for each step and the uniformity satisfy reference values, for example. However, this is not limited so.

FIG. 12 is a view illustrating an example of a display screen showing the load distribution and the result of each step. In a screen 70 illustrated in (A) of FIG. 12, the load distribution after each step ("STEP1" and "STEP2") and the load distribution after the whole steps are finished ("ALL") are shown. Here, in these load distributions, the color distributions corresponding to the pressing force obtained by the detecting unit 44 are displayed, for example. With this, the result of the application operation expressed by color can be obtained easily and accurately.

Here, in a screen 71 illustrated in (B) of FIG. 12, transitions of the pressing forces of "total", "STEP1" and "STEP2" are displayed in detail. For example, in the example of (B) of FIG. 12, "PASS" is displayed when the determined result satisfies the previously arbitrarily set acceptance standard and "FAIL" is displayed when the determined result does not satisfy the acceptance standard. With this, at which part the application force is not uniform can be easily grasped. The acceptance standard can be arbitrarily varied in accordance with a purpose of use.

(Relation Between each Application Operation and Evaluation)

Next, a relationship of each of the application operations and evaluations is explained. FIG. 13 is a view illustrating a relationship between each of the application operations and an in vitro SPF predicted value. In the example illustrated in FIG. 13, predicted values of the in vitro SPF to the applied surface are illustrated when varying the "application force (pressing force)", the "speed (seconds)" of each one stroke, the "plate support" and the "application time (seconds)" when applying the "Sample A" using the application operation evaluating apparatus 10. According to the predicted values, for example, it is illustrated that the predicted value of the in vitro SPF is significantly varied when the "application force" is varied. Conventionally, although the applied amount, the application time or the like may be regulated when evaluating an application method, the application force has not been considered as a variation factor.

Figure 14:
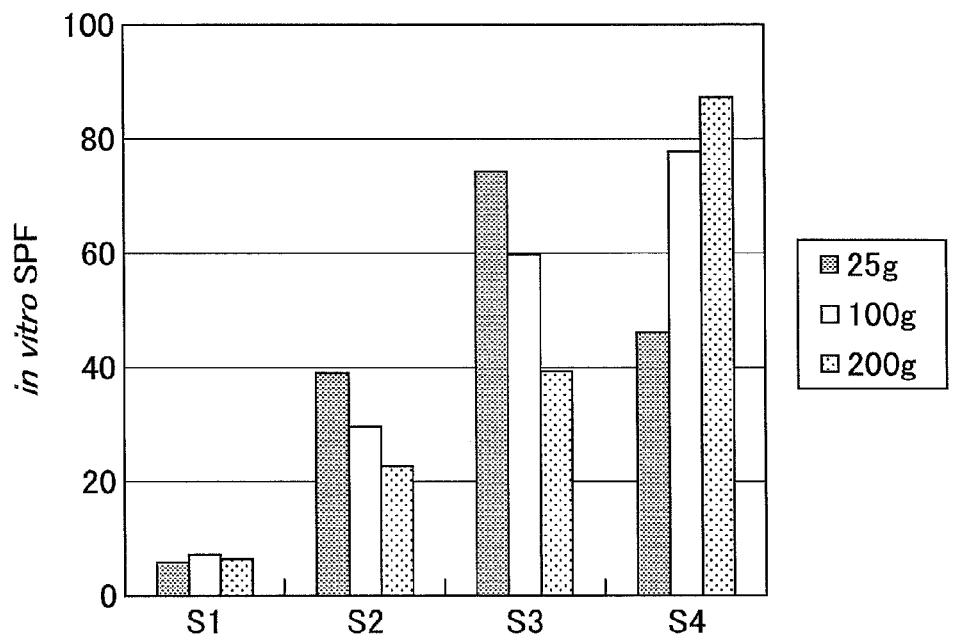
FIG. 14 is a view illustrating a relationship between an application force and an in vitro SPF predicted value of each sample.

FIG. 14 is a view illustrating a relationship between the application forces and in vitro SPF predicted values of each of the samples. Here, samples S1 to S4 are used. For the example illustrate in FIG. 14, the average value of the predicted values of the in vitro SPF to the applied surface is illustrated when the sample is applied by application forces of "25 g", "100 g" and "200 g" using the application operation evaluating apparatus 10. As illustrated in FIG. 14, when the application force is varied, the predicted value is also varied in all of the samples. As such, it can be understood that the application force influence on the predicted value of the in vitro SPF for all of the samples.

Figure 15:
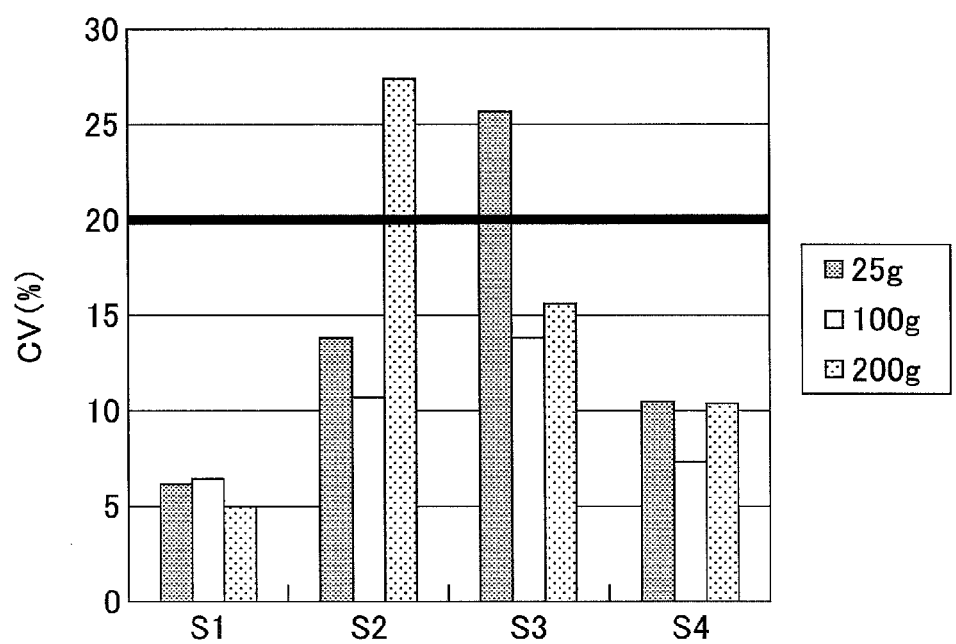
FIG. 15 is a view illustrating a relationship between the application force and a CV value (%) of the in vitro SPF predicted value of each of the samples.

FIG. 15 is a view illustrating a relationship between the application force and a CV value (%) of the in vitro SPF predicted value of each of the samples. For the example illustrated in FIG. 15, using the same samples (S1 to S4) as the samples of FIG. 14, CV values obtained from the predicted values of the in vitro SPF of FIG. 14 are illustrated. Generally, as the acceptance standard of repeatability, an effective value for the CV value is about less than or equal to 20%. It can be recognized that when the application force is "25 g" or "200 g", the effective value cannot be obtained for some samples.

The predicted value of the in vitro SPF is a result obtained by applying the sample on an application substrate SPF MASTER PA-01 (SHISEIDO CO LTD) with an amount of 2.00 mg/cart, and measuring using an SPF MASTER (SHISEIDO CO LTD).

Thus, by evaluating after standardizing the application operation such that the application force is "100 g" using the application operation evaluating apparatus 10, for example, it is possible to perform. an evaluation capable of actualizing the application with the uniform thickness by which the effective CV value can be obtained. Further, by varying the values that influence on the repeatability using the application operation evaluating apparatus 10, the value capable of further improving the repeatability can be obtained.

As described above, according to the embodiment, the repeatability regarding the application operation can be improved.

The individual constituents of the application operation evaluating apparatus 10 illustrated in FIG. 2 illustrate blocks of functional units, not hardware units. The individual constituents of the application operation evaluating apparatus 10 illustrated in FIG. 2 may be embodied by arbitrary combinations of hardware and software, typified by a CPU of an arbitrary computer, a memory, a program loaded in the memory so as to embody the constituents illustrated in the drawings, a storage unit for storing the program such as a hard disk, and an interface for network connection. It may be understood by those skilled in the art that methods and devices for the embodiment allow various modifications.

The present invention is not limited to the specifically disclosed embodiments, and numerous variations and modifications may be made without departing from the spirit and scope of the present invention.

The present application is based on and claims the benefit of priority of Japanese Priority Application No. 2012-047058 filed on Mar. 2, 2012, and Japanese Priority Application No. 2013-034865 filed on Feb. 25, 2013, the entire contents of which are hereby incorporated by reference.

What is claimed is:

1. An application operation evaluating apparatus, comprising:
a detecting unit that detects a measured pressing force of an application operation that uses a finger or a finger cot against an application target surface, based on pressing forces respectively obtained from a plurality of sensors that are provided at the application target surface, each of the sensors measuring load, the application target surface being provided with a plurality of sides;
an estimating unit that estimates a pressed position of the application operation against the application target surface based on a ratio of the pressing forces respectively applied to the sides of the application target surface, the pressing forces respectively being applied to the sensors, the application operation being performed over the entirety of a predetermined area of the application target surface, the predetermined period being a set length of time, the detecting unit detecting the measured pressing force for every predetermined period to obtain a plurality of the measured pressing forces for different positions over the entirety of the predetermined area of the application target surface, respectively, and the estimating unit estimating a plurality of the pressed positions corresponding to the plurality of the measured pressing forces, respectively, in accordance with the application operation over the entirety of the predetermined area of the application target surface;
a load distribution generating unit that generates a load distribution of the measured pressing forces and the respective pressed positions over the entirety of the predetermined area of the application target surface, respectively, in accordance with the application operation;
a display unit that displays the load distribution obtained by the load distribution generating unit on a load distribution display part corresponding to the predetermined area of the application target surface, and displays a pressing force transition display part in which the measured pressing forces obtained for the every predetermined period are displayed in accordance with time such that the horizontal axis indicates time and the vertical axis indicates pressing force with a previously set appropriate range of the pressing force; and
an evaluating unit that evaluates uniformity of application forces of the application operation for the different positions based on the measured pressing forces at the respective pressed positions.

2. The application operation evaluating apparatus according to claim 1,
wherein the load distribution generating unit generates a color distribution corresponding to the measured pressing forces.

3. The application operation evaluating apparatus according to claim 1, further comprising:
a storing unit that stores the measured pressing forces and the respective pressed positions in accordance with the application operation, the application operation including a plurality of strokes over the entirety of the predetermined area of the application target surface,
wherein the load distribution generating unit generates the load distribution using an accumulated value that is obtained by accumulating the measured pressing forces stored in the storing unit for each of the pressed positions.

4. The application operation evaluating apparatus according to claim 1,
wherein the display unit displays the measured pressing forces, the measured pressing forces varying in accordance with time detected by the detecting unit.

5. The application operation evaluating apparatus according to claim 4,
wherein the evaluating unit compares a peak value or an average value of the measured pressing forces within a predetermined time with a previously set appropriate value and evaluates the application operation based on the compared result.

6. The application operation evaluating apparatus according to claim 1,
wherein the detecting unit detects the measured pressing forces resulting from a predetermined application operation by which skin lotion provided on the predetermined area of the application target surface is applied to the entirety of the predetermined area of the application target surface.

7. A non-transitory computer-readable recording medium having recorded thereon an application operation evaluating program that causes a computer to function as the units of the application operation evaluating apparatus according to claim 1.

8. The application operation evaluating apparatus according to claim 1,
wherein each of the sensors is configured to measure weight.

9. The application operation evaluating apparatus according to claim 1, further comprising:
an output unit that outputs a sound,
wherein the display unit displays a screen including an operation display part that includes a play button which causes the output unit to output a starting sound that indicates starting of the application operation, and then output an indicating sound for indicating a timing to match the application operation to a speed of each stroke of the application operation.

10. The application operation evaluating apparatus according to claim 1,
wherein the application operation includes applying a first sequence of strokes in a first predetermined direction.

11. The application operation evaluating apparatus according to claim 10,
wherein the application operation further includes, after applying the first sequence of strokes, applying a second sequence of strokes in a second predetermined direction, that is perpendicular to the first predetermined direction.

12. The application operation evaluating apparatus according to claim 1,
wherein the application operation includes drawing small circles on the predetermined area of the application target surface.

13. The application operation evaluating apparatus according to claim 1,
wherein the appropriate range of the pressing force is displayed as a shaded band along the time in the pressing force transition display part and the measured pressing forces that are within the appropriate range are overlapped on the shaded band.

14. An application operation evaluating method, comprising:
detecting a measured pressing force of an application operation that uses a finger or a finger cot against an application target surface, based on pressing forces respectively obtained from a plurality of sensors that are provided at the application target surface, each of the sensors measuring load, the application target surface being provided with a plurality of sides;
estimating a pressed position of the application operation against the application target surface based on a ratio of the pressing forces respectively applied to the sides of the application target surface, the pressing forces respectively being applied to the sensors,
the application operation being performed over the entirety of a predetermined area of the application target surface,
the predetermined period being a set length of time,
the measured pressing force being detected for every predetermined period to obtain a plurality of the measured pressing forces for different positions over the entirety of the predetermined area of the application target surface, respectively, in the detecting and the plurality of pressed positions corresponding to the plurality of the measured pressing forces, respectively, being estimated in the estimating, in accordance with the application operation over the entirety of the predetermined area of the application target surface;
generating a load distribution of the measured pressing forces and the respective pressed positions over the entirety of the predetermined area of the application target surface, respectively, in accordance with the application operation;
displaying the load distribution obtained in the generating on a load distribution display part corresponding to the predetermined area of the application target surface, and displays a pressing force transition display part in which the measured pressing forces obtained for the every predetermined period are displayed in accordance with time such that the horizontal axis indicates time and the vertical axis indicates pressing force with a previously set appropriate range of the pressing force; and
evaluating uniformity of application forces of the application operation for the different positions based on the measured pressing forces at the respective pressed positions.

15. The application operation evaluating method according to claim 14,
wherein in the generating, a color distribution corresponding to the measured pressing forces is generated.

16. The application operation evaluating method according to claim 14, further comprising:
storing the measured pressing forces and respective pressed positions in accordance with the application operation, the application operation including a plurality of strokes over the entirety of the predetermined area of the application target surface,
wherein in the generating, generating the load distribution using an accumulated value that is obtained by accumulating the measured pressing forces stored in the storing for each of the pressed positions.

17. The application operation evaluating method according to claim 14,
wherein in the displaying, the measured pressing forces, the measured pressing forces varying in accordance with time detected in the detecting are displayed.

18. The application operation evaluating method according to claim 17,
wherein in the evaluating, a peak value or an average value of the measured pressing forces within a predetermined time is compared with a previously set appropriate value and the application operation is evaluated based on the compared result.

19. The application operation evaluating method according to claim 14,
wherein in the detecting, the measured pressing forces resulting from a predetermined application operation, by which skin lotion provided on the predetermined area of the application target surface is applied to the entirety of the predetermined area of the application target surface, are detected.

20. The application operation evaluating method according to claim 14,
wherein each of the sensors is configured to measure weight.

* * * * *